(12) United States Patent
Suzuki et al.

(10) Patent No.: US 11,538,315 B2
(45) Date of Patent: Dec. 27, 2022

(54) TACTILE SENSATION PRESENTING DEVICE AND TACTILE SENSATION PRESENTING SYSTEM

(71) Applicant: SONY CORPORATION, Tokyo (JP)

(72) Inventors: Hiroyuki Suzuki, Tokyo (JP); Ryuta Horie, Tokyo (JP)

(73) Assignee: SONY CORPORATION, Tokyo (JP)

( * ) Notice: Subject to any disclaimer, the term of this patent is extended or adjusted under 35 U.S.C. 154(b) by 5 days.

(21) Appl. No.: 17/250,682

(22) PCT Filed: Aug. 22, 2019

(86) PCT No.: PCT/JP2019/032918
§ 371 (c)(1),
(2) Date: Feb. 18, 2021

(87) PCT Pub. No.: WO2020/045250
PCT Pub. Date: Mar. 5, 2020

(65) Prior Publication Data
US 2021/0183216 A1    Jun. 17, 2021

(30) Foreign Application Priority Data
Aug. 29, 2018  (JP) .............................. JP2018-160693

(51) Int. Cl.
*G08B 6/00* (2006.01)
*G06F 3/01* (2006.01)

(52) U.S. Cl.
CPC ............... *G08B 6/00* (2013.01); *G06F 3/016* (2013.01)

(58) Field of Classification Search
CPC .......... G08B 6/00; A61B 34/76; A61B 34/37; G06F 3/016; B25J 13/025
See application file for complete search history.

(56) References Cited

U.S. PATENT DOCUMENTS

| 5,451,924 A | 9/1995 | Massimino et al. |
| 5,619,180 A | 4/1997 | Massimino et al. |
| 6,088,017 A | 7/2000 | Tremblay et al. |

(Continued)

FOREIGN PATENT DOCUMENTS

| CN | 102581853 A | 7/2012 |
| CN | 104840253 A | 8/2015 |

(Continued)

OTHER PUBLICATIONS

International Search Report and Written Opinion of PCT Application No. PCT/JP2019/032918 dated Oct. 29, 2019, 10 pages of ISRWO.

(Continued)

*Primary Examiner* — John A Tweel, Jr.
(74) *Attorney, Agent, or Firm* — Chip Law Group

(57) ABSTRACT

There is provided a tactile sensation presenting device including a plurality of tactile sensation presenting units that presents a tactile sensation based on control information, and a control unit that generates the control information which is different for each of the plurality of tactile sensation presenting units, based on information which is generated by an operation tool and is related to contact between the operation tool and an object. The control unit further provides the control information to each of the plurality of tactile sensation presenting units.

17 Claims, 16 Drawing Sheets

(56) References Cited

U.S. PATENT DOCUMENTS

| | | | |
|---|---|---|---|
| 8,332,072 B1 | 12/2012 | Schaible et al. | |
| 8,519,948 B2 * | 8/2013 | Cruz-Hernandez | G06F 3/016 345/156 |
| 11,266,471 B2 * | 3/2022 | Schaible | B25J 13/025 |
| 2004/0116906 A1 * | 6/2004 | Lipow | A61B 34/76 606/1 |
| 2010/0179587 A1 | 7/2010 | Grant et al. | |
| 2012/0154131 A1 | 6/2012 | Lee et al. | |
| 2013/0197538 A1 | 8/2013 | Schaible et al. | |
| 2013/0197697 A1 | 8/2013 | Schaible et al. | |
| 2013/0211418 A1 | 8/2013 | Lim et al. | |
| 2014/0336669 A1 | 11/2014 | Park | |
| 2015/0230869 A1 | 8/2015 | Shim et al. | |
| 2017/0225337 A1 | 8/2017 | Schaible et al. | |
| 2018/0024696 A1 | 1/2018 | Lee et al. | |
| 2019/0282309 A1 | 9/2019 | Schaible et al. | |
| 2021/0228291 A1 | 7/2021 | Schaible et al. | |

FOREIGN PATENT DOCUMENTS

| | | |
|---|---|---|
| EP | 2468464 A1 | 6/2012 |
| EP | 2907467 A1 | 8/2015 |
| JP | 60-209902 A | 10/1985 |
| JP | 06-209902 A | 8/1994 |
| JP | 08-090472 A | 4/1996 |
| JP | 08-254472 A | 10/1996 |
| JP | 2000-501033 A | 2/2000 |
| JP | 2007-316936 A | 12/2007 |
| JP | 2010-533032 A | 10/2010 |
| JP | 2012-131024 A | 7/2012 |
| JP | 2012-515048 A | 7/2012 |
| JP | 4982877 B2 | 7/2012 |
| JP | 2015-150425 A | 8/2015 |
| KR | 10-2012-0069980 A | 6/2012 |
| KR | 10-2013-0092189 A | 8/2013 |
| KR | 10-2014-0132649 A | 11/2014 |
| KR | 10-2015-0097238 A | 8/2015 |
| WO | 97/20305 A1 | 6/1997 |
| WO | 2007/119603 A1 | 10/2007 |
| WO | 2010/083060 A1 | 7/2010 |

OTHER PUBLICATIONS

Extended European Search Report of EP Application No. 19854929.7, dated Aug. 19, 2021, 09 pages.

* cited by examiner

TACTILE SENSATION PRESENTING DEVICE AND TACTILE SENSATION PRESENTING SYSTEM

CROSS REFERENCE TO RELATED APPLICATIONS

This application is a U.S. National Phase of International Patent Application No. PCT/JP2019/032918 filed on Aug. 22, 2019, which claims priority benefit of Japanese Patent Application No. JP 2018-160693 filed in the Japan Patent Office on Aug. 29, 2018. Each of the above-referenced applications is hereby incorporated herein by reference in its entirety.

TECHNICAL FIELD

The present disclosure relates to a tactile sensation presenting device and a tactile sensation presenting system.

BACKGROUND ART

In recent years, as a surgical system used for performing endoscopic surgery, a master-slave type system (also referred to as a master-slave system herein below) is known, which is capable of approaching an affected area without making a long incision in a body of a patient. In such a master-slave system, an operator (user), such as a physician, operates a master device which includes an input interface, and in accordance with the operation of the master device performed by the operator, a slave device, which includes such a medical instrument as forceps or tweezers, is operated by remote control. The slave device is structured as an arm device of which end portion holds the medical instrument, for example, and the position or attitude of the medical instrument can be changed inside the abdominal cavity.

In the case of this master-slave system, when the contact state between the patient and the medical instrument is not detected, the operator may cause damage to the biotissue of the patient without noticing that the medical instrument is in contact with the patient. Therefore a technique to detect the contact state between the patient and the medical instrument on the slave device side and to feedback the contact state to the operator on the master device side was developed. An example of this technique is a method of disposing a sensor, which measures information on the contact state between the patient and the medical instrument, on the slave device, sending the information on the contact state measured by this sensor to the master device, and presenting a tactile sensation to the operation using vibration or the like on the master device side. As a technique related to this method, the following PTL 1, for example, discloses a technique to allow the operator to perceive the tactile sensation more easily by amplifying a signal on distortion which is detected when the patient and the medical instrument contact.

CITATION LIST

Patient Literature

[PTL1]
Japanese Translation of PCT Application No. 2010-533032

SUMMARY

Technical Problem

In the above mentioned technique, however, the tactile perceptual characteristic of a human (also referred to as a user herein below) is not considered when the tactile sensation presenting device amplifies the signal related to the contact. Therefore in the case where the tactile sensation presented by the amplified signal does not satisfy the tactile perceptual characteristic of a human, the user may have difficulty in perceiving the presented tactile sensation, even if the signal related to the contact is amplified using the above mentioned technique.

With the foregoing in view, the present disclosure provides new and improved tactile sensation presenting device and tactile sensation presenting system, which are capable of presenting a tactile sensation that the user can perceive more easily.

Solution to Problem

According to the present disclosure, a tactile sensation presenting device is provided, including; a plurality of tactile sensation presenting units configured to present a tactile sensation based on control information; and a control unit configured to generate the control information, which is different for each of the plurality of tactile sensation presenting units, based on information which is generated by an operation tool and is related to contact between the operation tool and an object, and to provide the control information to each of the plurality of tactile sensation presenting units.

Further, according to the present disclosure, a tactile sensation presenting system is provided, including: a tactile sensation presenting device which includes a plurality of tactile sensation presenting units configured to present a tactile sensation based on control information, and a control unit configured to generate the control information, which is different for each of the plurality of tactile sensation presenting units, based on information which is generated by an operation tool and is related to contact between the operation tool and an object, and to provide the control information to each of the plurality of tactile sensation presenting units; a master device in which the tactile sensation presenting device is disposed; and a slave device in which the operation tool is disposed and which operates in accordance with operation of the master device by a user.

Advantageous Effects of Invention

As described above, according to the present disclosure, a tactile sensation that the user can more easily perceive can be presented. It should be noted that the above mentioned effect is not restrictive, and any effect indicated in the present description or a different effect that may be grasped based on the present description may be implemented along with or instead of the above mentioned effect.

DESCRIPTION OF EMBODIMENTS

Figure 1:
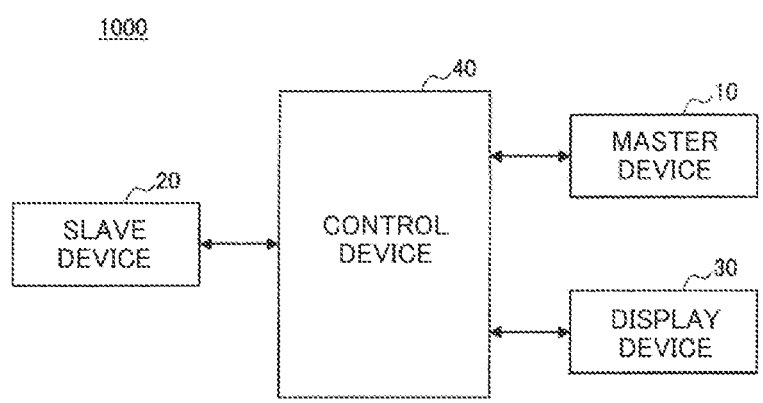
FIG. 1 is a diagram depicting a general configuration of a master-slave system according to an embodiment of the present disclosure.

Embodiments of the present disclosure will now be described with reference to the accompanying drawings. In the present description and drawings, composing elements having substantially a same functional configuration are denoted with a same reference sign, and redundant explanation thereof is omitted.

Description will now be performed according to the following sequence.
1. Overview
2. Embodiments of disclosure
2-1. Configuration of master-slave system
2-2. Configuration of tactile sensation presenting device
3. Modifications
3-1. Modification 1
3-2. Modification 2
3-3. Modification 3
3-4. Modification 4
3-5. Modification 5
4. Hardware configuration example
5. Conclusion 1. Overview In recent years, as a surgical system that is used for performing endoscopic surgery, a master-slave type system (also referred to as a master-slave system herein below) is known, which is capable of approaching an affected area without making a long incision in a body of a patient. In such a master-slave system, an operator (user), such as a physician, operates a master device which includes an input interface, and in accordance with the operation of the master device performed by the operator, a slave device, which includes such a medical instrument as forceps or tweezers, is operated by remote control. The slave device is structured as an arm device of which end portion holds the medical instrument, for example, and the position or the attitude of the medical instrument can be changed inside the abdominal cavity.

In the case of this master-slave system, when the contact state between the patient and the medical instrument is not detected, the operator may cause damage to the biotissue of the patient without noticing that the medical instrument is in contact with the patient. Therefore in some cases, a method called hand-assisted laparoscopic surgery (HALS) is used, that is, a method of the operator inserting their hand through a hole that is opened separately from the hole for inserting the medical instrument, and performing surgery while directly touching the tissue by hand. With this method, however, the operator can perform surgery while perceiving the tactile sensation, but the degree of invasiveness into the abdominal cavity is higher than an ordinary endoscopic surgery that does not use HALS. Hence a technique of detecting the contact state between the patient and the medical instrument on the slave device side and feeding back the contact state to the operator on the master device side was developed. An example of the method using this technique is disposing a sensor, which measures information on the contact state between the patient and the medical instrument, in the slave device, transmitting the information on the contact state measured by this sensor to the master device, and presenting the tactile sensation to the operator on the master device side using vibration or the like. Further, related to this method, a technique of increasing the level of sensitivity of the tactile sensation presented to the operator by amplifying a signal related to the contact detected when the patient and the medical instrument contact, for example, was disclosed.

In the above mentioned technique, however, the tactile perceptual characteristic of a human (also referred to as a user herein below) is not considered when the tactile sensation presenting device amplifies the signal related to the contact. Therefore in the case where the tactile sensation presented by the amplified signal does not satisfy the tactile perceptual characteristic of a human, the user may have difficulty in perceiving the presented tactile sensation, even if the signal related to the contact is amplified using the above mentioned technique. For example, in the case where the operator operates the master device such that the medical instrument is slowly pushed into the affected area of the patient with weak force, the signal detected by the contact between the medical instrument and the affected area becomes a weak signal in accordance with the magnitude of the force inputted by the operator. Even if this weak signal is amplified using the above mentioned technique, the operator has difficulty in perceiving the presented tactile sensation unless the amplified signal satisfies the tactile perceptual characteristic of a human.

The master-slave system according to the embodiment of the present disclosure was invented with the above aspect in view, and is capable of presenting a tactile sensation that the user can perceive more easily. Each embodiment of the present disclosure having this effect will now be sequentially described in detail.

2. Embodiments of Disclosure 2-1. Configuration of Master-Slave System

Figure 2:
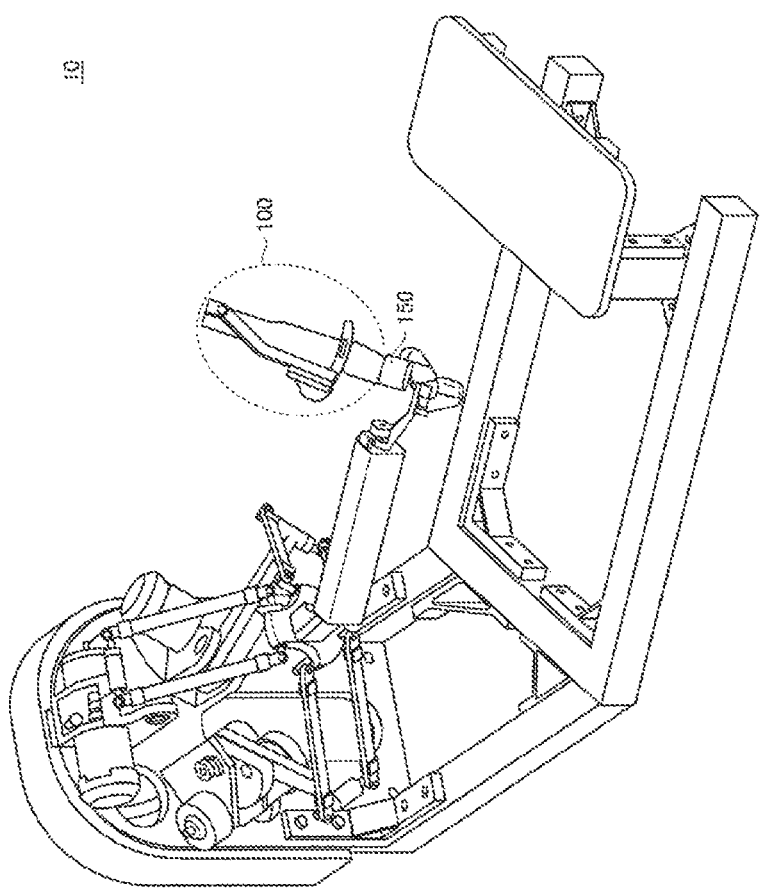
FIG. 2 is an explanatory drawing of an example of a master device according to the embodiment.
Figure 3:
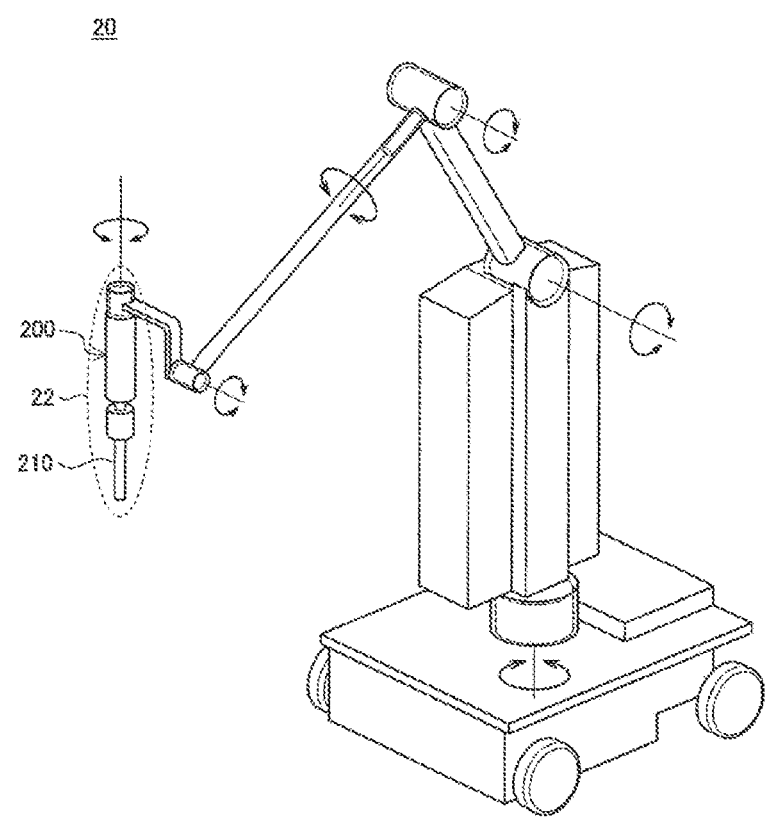
FIG. 3 is an explanatory drawing of an example of a slave device according to the embodiment.

The configuration of the master-slave system according to an embodiment of the present disclosure will be described with reference to FIG. 1 to FIG. 3. FIG. 1 is a diagram depicting a general configuration of the master-slave system according to the embodiment of the present disclosure. FIG. 2 is an explanatory drawing of an example of a master device according to the embodiment of the present disclosure. FIG. 3 is an explanatory drawing of an example of a slave device according to the embodiment of the present disclosure.

As illustrated in FIG. 1, the master-slave system 1000 according to the embodiment of the present disclosure is a master-slave type surgery system which includes a master device 10, a slave device 20, an output device 30 and a control device 40.

(1) Master Device 10

The master device 10 is a device on the master side of the master-slave system 1000. For example, the master device 10 may be a robot having one joint or two or more joints, including a passive joint, and a link connected to a joint (robot having a link mechanism which includes a passive joint). The passive joint refers to a joint that is not driven by a motor, an actuator, or the like.

In the example illustrated in FIG. 2, the master device 10 includes a tactile sensation presenting device 100 which is disposed in the link connected to the passive joint, and a force sensor 150 that measures the force applied to the tactile sensation presenting device 100. Examples of the force sensor 150 according to the present embodiment are, "an arbitrary type of force sensor, such as a type that uses a strain gauge", "an arbitrary type of tactile sensor, such as a type that acquires a tactile sense by measuring vibration using a piezoelectric element, a microphone, or the like", and other arbitrary sensors that can measure the force applied to the tactile sensation presenting device 100. Further, the master device 10 includes a motion sensor to measure the motion of the joint, for example, for each position corresponding to the joints.

In the present embodiment, the master device 10 is used for operating the slave device 20. For example, the master device 10 includes the tactile sensation presenting device 100 which is an input interface of the master device 10. The user moves a position of an operation tool 210 of the later mentioned slave device 20 by the operation to move the position of the tactile sensation presenting device 100 (operation by remote control). It should be noted that the operation tool 210 according to the present embodiment is an operation target of the master device 10, and is a tool operated as the user operates the master device 10.

While FIG. 2 indicates an example where the tactile sensation presenting device 100 disposed in the master device 10 is a stylus type operation device, the tactile sensation presenting device 100 according to the present embodiment is not limited to the example illustrated in FIG. 2. An example of the tactile sensation presenting device 100 according to the present embodiment is an arbitrarily-shaped operation device, such as a glove type operation device. Furthermore, the tactile sensation presenting device 100 according to the present embodiment may be an arbitrary operation device that can be applied to a haptic device. The master device 10 may have a structure in which the tactile sensation presenting device 100 is replaceable. It should be noted that the configuration of the master device 10 according to the present embodiment is not limited to the example illustrated in FIG. 2, but may be an arbitrary configuration.

The tactile sensation presenting device 100 also includes a tactile sensation presenting unit to present a vibration, which is generated when the operation tool 210 of the slave device 20 comes into contact with an object, to the user as a tactile sensation. The tactile sensation presenting unit is implemented by a vibration device, for example. For the vibration device, a voice coil motor (VCM) type vibration actuator, for example, is used. For the vibration device, a linear resonant actuator (LRA) or a piezoelectric element may be used.

The object refers to a contact target of the operation tool 210. Examples of the object are a patient or a part of the body of a human or an animal. A part of the body of a human is skin or an internal organ, for example. The object is not limited to these examples but may be an arbitrary object. In the following, an example where the object is a patient will be described.

(2) Slave Device 20

The slave device 20 is a device on the slave side of the master-slave system 1000. For example, the slave device 20 may be a robot having one active joint or two or more active joints, and a link connected to an active joint (robot having a link mechanism which includes an active joint) in order to move in accordance with the input operation performed on the master device 10. The active joint refers to a joint that is driven by a motor, an actuator, or the like.

The slave device 20 also includes a motion sensor to measure the motion of an active joint at a position corresponding to each active joint. For the motion sensor, an encoder is used, for example. Further, the slave device 20 includes a driving mechanism to drive an active joint at a position corresponding to each active joint. For the driving mechanism, a motor and a driver are used, for example. This driving mechanism may be controlled by the control device 40 which will be described later.

In the example illustrated in FIG. 3, a medical instrument 200 is disposed in an end unit 22, which is an end portion of an arm of the slave device 20. In the end portion of the medical instrument 200, the operation tool 210 which comes into contact with the patient is further disposed. The user remotely controls the position of the operation tool 210 by operating the master device 10.

Furthermore, the slave device 20 may include various sensors (for example, a strain sensor, a force sensor, a vibration sensor, an origin sensor, a limit sensor, an encoder, a microphone, an acceleration sensor, and the like) in the medical instrument 200. For example, the slave device 20 includes a sensor, to detect a contact force with an object, in the medical instrument 200. Specifically, the slave device 20 may include fiber bragg grating (FBG). FBG is one optical fiber sensing technique. FBG, which is an optical fiber, is thin and light and has high durability. Therefore FBG is suitable for a small diameter device, such as medical forceps. FBG is also capable of detecting only the force applied to the end portion, such as medical forceps, without detecting the mechanism vibration of an actuator or the like that is used for driving the medical forceps or the like. Thereby the tactile sensation presenting device 100 can present a more accurate tactile sensation to the user. Furthermore, the slave device 20 includes a vibration sensor in the medical instrument 200, for example. This vibration sensor measures the vibration propagating through the operation tool 210 when the operation tool 210 comes into contact with the patient. The slave device 20 also includes a microphone in the medical instrument 200, for example. This microphone measures vibration propagating through the air when the operation tool 210 comes into contact with the patient. The positions where various sensors mentioned above are disposed are not especially limited, and various sensors may be disposed in arbitrary positions of the medical instrument 200.

The slave device 20 illustrated in FIG. 3 is an example, and the configuration of the slave device 20 according to the present embodiment is not limited to the example in FIG. 3.

(3) Output Device 30

The output device 30 outputs the later mentioned output information that is inputted from the control device 40. For example, the output device 30 may be such a display device as a stationary type display or a head mounted display (HMD) which is mounted on the head of the user. In the case where image information is inputted from the control device 40 as output information, the output device 30 displays the image on the display device. The output device 30 may also be such a sound output device as a speaker and headphone. In the case where sound information is inputted from the control device 40 as output information, the output device 30 outputs the sound from this sound output device.

The device that can be used as the output device 30 is not limited to the above mentioned examples, but may be an arbitrary device.

(4) Control Device 40

The control device 40 controls each of the other devices included in the master-slave system 1000. For example, the control device 40 performs control related to the operation of the master device 10. Specifically, the control device 40 performs control to send information related to the contact, which is received from the slave device 20, to the master device 10. The information related to the contact refers to information acquired when the operation tool 210 and the patient contact. The information related to the contact includes frequency of vibration and displacement amount that is generated by the contact between the operation tool 210 and the patient. Furthermore, the information related to the contact may include a contact force generated when the operation tool 210 and the patient contact.

Further, the control device 40 controls operation of the slave device 20. Specifically, the control device 40 receives information to indicate the instruction to operate the arm of the slave device 20, from the master device 10, and based on the received information, the control device 40 controls the operation of the arm of the slave device 20. The information to indicate the instruction to operate the arm is inputted by the user operating the tactile sensation presenting device 100 of the master device 10.

The control device 40 controls output in the output device 30. Specifically, the control device 40 receives an image (still image/moving image), which is captured by a camera disposed in the operation tool 210 of the arm of the slave device 20, from the slave device 20, transmits this image to the output device 30, and causes the output device 30 to output this image.

The control device 40 is connected to each of the other devices included in the master-slave system 1000 using an arbitrary communication system, and transmits/receives information relates to control to/from each of the other devices via communication.

2-2. Configuration of Tactile Sensation Presenting Device

A configuration example of the tactile sensation presenting device according to the embodiment of the present disclosure will be described with reference to FIG. 4 to FIG. 8.

<2-2-1. External Configuration Example of Tactile Sensation Presenting Device>

(Basic Configuration of Tactile Sensation Presenting Device)

Figure 4:
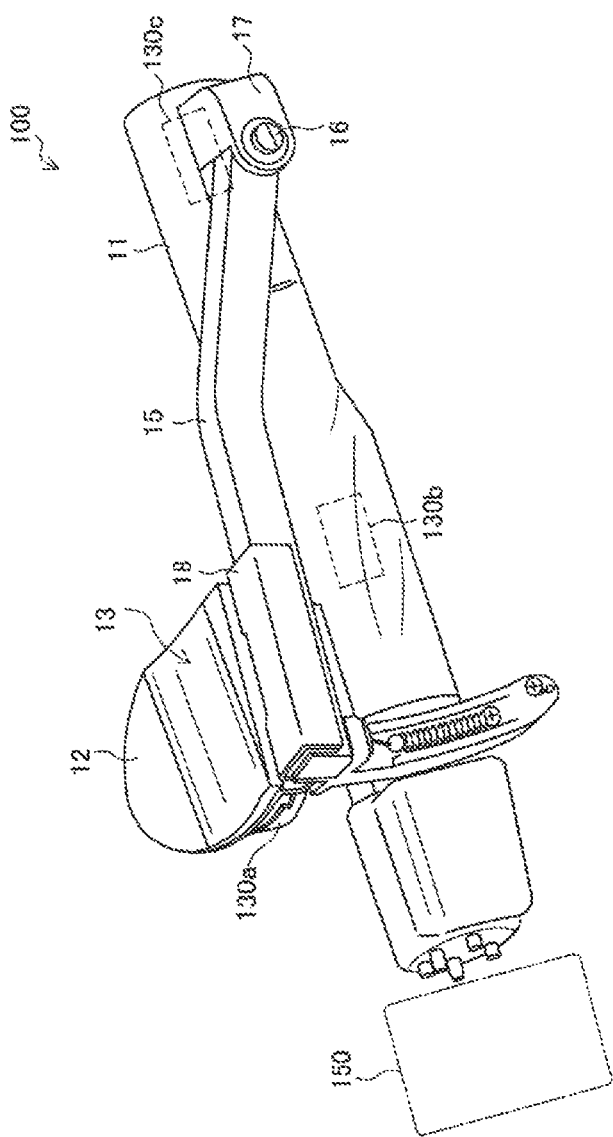
FIG. 4 is a perspective view illustrating an external configuration of a tactile sensation presenting device according to the embodiment.

FIG. 4 is a perspective view illustrating an external configuration of the tactile sensation presenting device 100 according to the embodiment of the present disclosure. The tactile sensation presenting device 100 includes a casing 11 that encloses a motor (not illustrated) and an encoder (not illustrated). The casing 11 generally has a long stick shape that is easy for the user to hold. In other words, the tactile sensation presenting device 100 has a so called stylus type grip interface. This tactile sensation presenting device 100 is installed in an arm unit of the master device 10 on the front end side. A force sensor 150 is disposed in a connection portion between the front end side of the tactile sensation presenting device 100 and the arm unit.

A rotation shaft member 16 is disposed on the rear end side of the casing 11. Both ends of the rotation shaft member 16 are supported by a bearing 17 and the casing 11. A master frame 15, which is a frame unit, is rotatably connected to the rotation shaft member 16 with the rotation shaft member 16 at the center.

The master frame 15 is a long member that is disposed on one side face side of the tactile sensation presenting device 100 along the longer side, and extends along the direction crossing the shaft direction of the rotation shaft member 16. At an appropriate position on the front end side of the master frame 15, a contact unit 12, having a surface that extends along the longer direction of the tactile sensation presenting device 100, is disposed so as to intersect with the rotating direction of the master frame 15. The contact unit 12 is installed on the master frame 15 via a support unit 18. The contact unit 12 may include a placing unit 13 on which the user places their index finger, for example. The placing unit 13 may have an arched concave shape so as to fit with the shape of the finger of the operator. The operator holds the tactile sensation presenting device 100 as if gripping a pen for writing, and places their index finger on the placing unit 13, whereby the master frame 15 can be rotated.

The tactile sensation presenting device 100 includes a plurality of tactile sensation presenting units 130. For example, as illustrated in FIG. 4, the tactile sensation presenting device 100 includes a tactile sensation presenting unit 130a near the contact unit 12. For example, a tactile sensation presenting unit 130a may be disposed in the support unit 18, on the rear surface side of the surface where the contact unit 12 is disposed. In the present embodiment, for the tactile sensation presenting unit 130a, a voice coil motor type vibration actuator is used, but another vibration generation source may be used. The tactile sensation presenting device 100 also includes a tactile sensation presenting unit 130b and a tactile sensation presenting unit 130c, as illustrated in FIG. 4. The positions where the tactile sensation presenting unit 130b and the tactile sensation presenting unit 130c are disposed are in the vicinity of the positions where the casing 11 and the user contact, and are inside the casing 11. These tactile sensation presenting units 130 generate vibration that is transferred to the finger of the operator that is placed on the placing unit 13, and presents this vibration to the operator as a vibration corresponding to the information related to the contact between the slave device 20 and the patient (hereafter also referred to as tactile sensation vibration).

One characteristic of the tactile sensation presenting device 100 according to the embodiment of the present disclosure includes the plurality of tactile sensation presenting units 130. This is due to the perceptual characteristic of a human, therefore the perceptual characteristic of a human will now be described in detail.

(Perceptual Characteristic of a Human)

Figure 5:
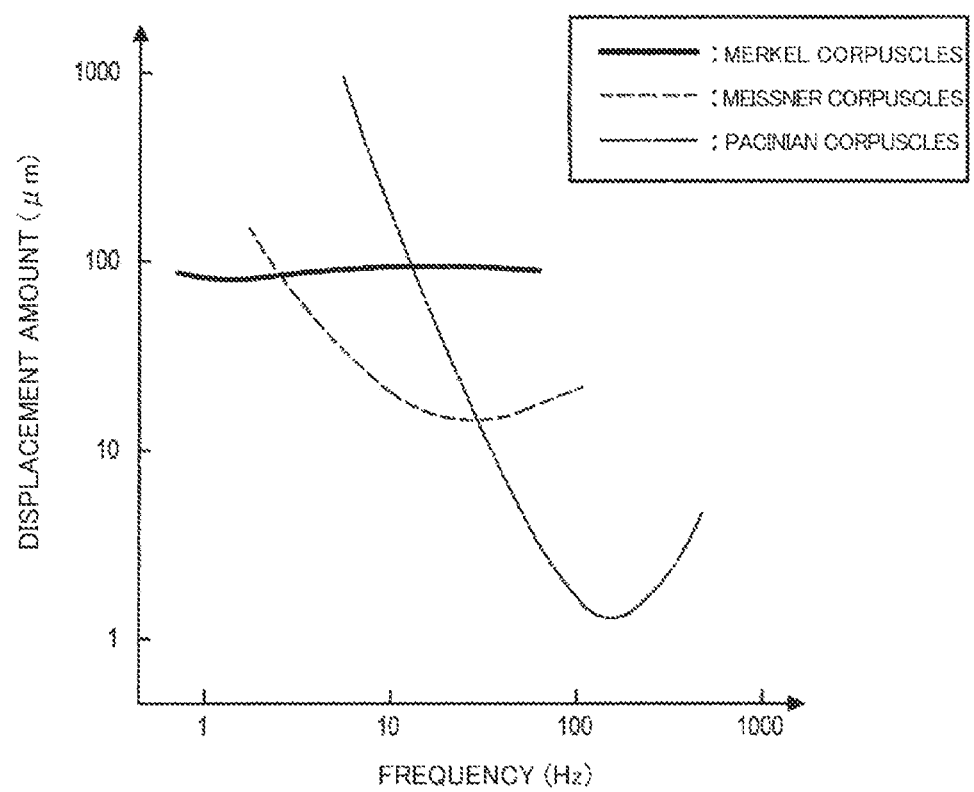
FIG. 5 is a graph for explaining the tactile perceptual characteristic of a human.

The perceptual characteristic of humans will be described with reference to FIG. 5. FIG. 5 is a graph for explaining the tactile perceptual characteristic of a human. The abscissa of the graph in FIG. 5 indicates a frequency (Hz) of vibration applied to a human, and the ordinate indicates a displacement amount (μm) of the vibration applied to a human.

There are many tactile receptors under human skin to detect tactile sensation. There are a plurality of types of tactile receptors, such as Meissner corpuscles, Merkel corpuscles, Pacinian corpuscles and Ruffini corpuscles. The Meissner corpuscles are tactile receptors existing in the papillary dermis. The Merkel corpuscles are tactile receptors existing in a deepest part of the epidermis. The Pacinian corpuscles are tactile receptors existing inside the subcutaneous tissue and in the deep layers of the dermis. The Ruffini corpuscles are tactile receptors existing in a relatively deep portion of the dermis. The response characteristics of these four types of tactile receptors are classified into three: fast adapting (FA), rapidly adapting (RA) and slowly adapting (SA). FA and RA indicate that the tactile receptor has a fast response characteristic, and SA indicates that the tactile receptor has a slow response characteristic.

The detectable vibration of each tactile receptor is different in accordance with the response characteristic of each tactile receptor. The graph in FIG. 5 indicates the thresholds related to the detectable vibration of each tactile receptor (also referred to as detection threshold herein below below). In the graph in FIG. 5, the solid line indicates a detection threshold of the Merkel corpuscles, the broken line indicates a detection threshold of the Meissner corpuscles, and the chain line indicates a detection threshold of the Pacinian corpuscles. A detection threshold of the Ruffini corpuscles is the same as the detection threshold of the Merkel corpuscles, hence indication thereof is omitted. The detection threshold indicates the minimum vibration displacement amount that the tactile receptor of a human can detect when a predetermined frequency of vibration is presented to a human. In other words, in the case where the displacement amount of the predetermined frequency of vibration presented to the user is greater than the detection threshold, the user can detect the presented vibration. In the case where the displacement amount of the predetermined frequency of vibration presented to the user is smaller than the detection threshold, the user cannot detect the presented vibration.

Specifically, as indicated in FIG. 5, in the case where the frequency of the vibration presented to the user is 1 Hz, the Merkel corpuscles detect the vibration if the displacement amount of the vibration is at least 100 μm, therefore the user can perceive the tactile sensation. In the case where the frequency of the vibration presented to the user is 100 Hz, the Pacinian corpuscles detect the vibration if the displacement amount of the vibration is at least 5 μm, therefore the user can perceive the tactile sensation.

As indicated in FIG. 5, the detection threshold of each tactile receptor is different. Furthermore, a quantity, displacement and the like of each tactile receptor differ depending on a position where tactile sensation is presented by the tactile sensation presenting unit 130. Therefore in some cases the user may perceive the tactile sensation differently depending on the region where the tactile sensation is presented. As a consequence, it is preferable that the tactile sensation presenting unit 130 presents tactile sensation that is different depending on the region where tactile sensation is presented to the user. By the tactile sensation presenting unit 130 presenting tactile sensation that is different depending on the region, the user can perceive the tactile sensation that is closer to the tactile sensation perceived when the user actually holds a medical instrument.

(Number and Positions of Tactile Sensation Presenting Units)

Figure 6:
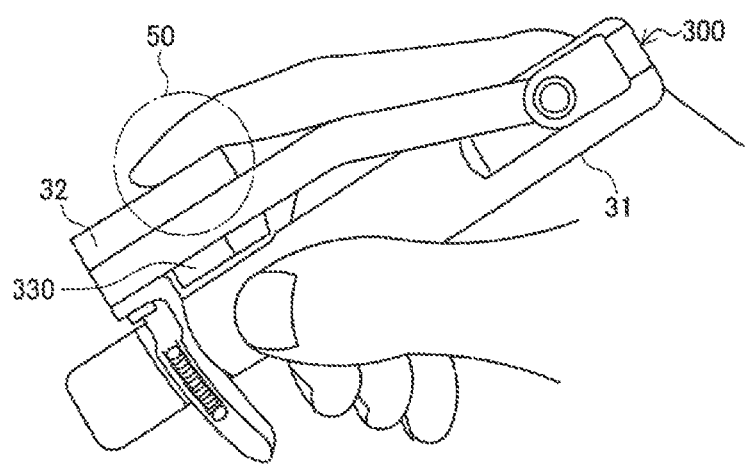
FIG. 6 is an explanatory drawing of an example of holding a tactile sensation presenting device according to a comparative example.
Figure 7:
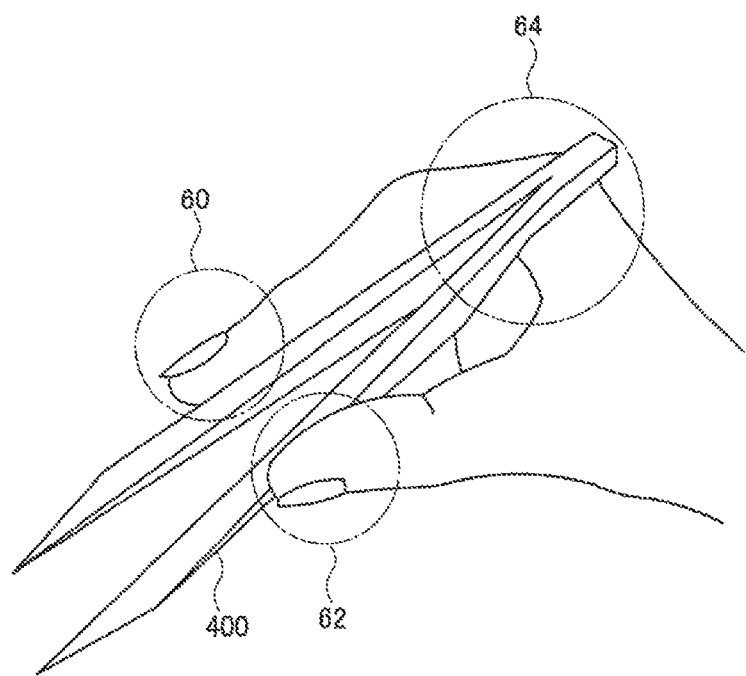
FIG. 7 is an explanatory drawing of an example of holding tweezers according to a comparative example.
Figure 8:
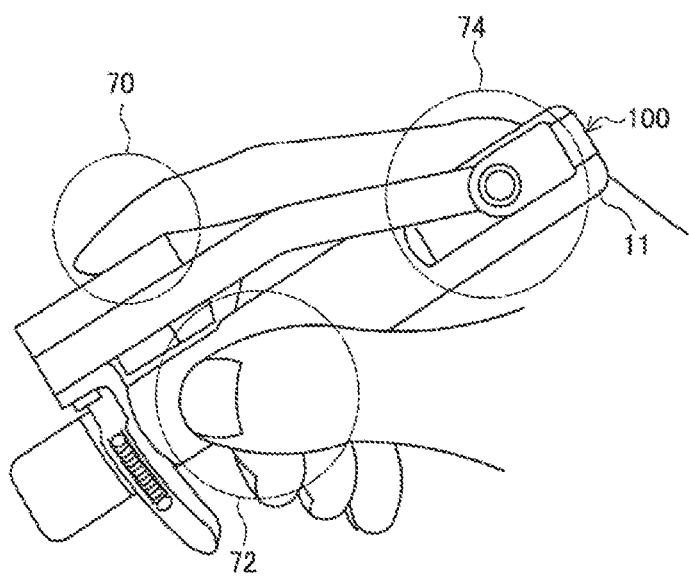
FIG. 8 is an explanatory drawing of an example of holding the tactile sensation presenting device according to the embodiment of the present disclosure.

A number and positions of the tactile sensation presenting units 130 will be described with reference to FIG. 6 to FIG. 8. FIG. 6 is an explanatory drawing of an example of holding a tactile sensation presenting device according to a comparative example. FIG. 7 is an explanatory drawing of an example of holding tweezers according to a comparative example. FIG. 8 is an explanatory drawing of an example of holding the tactile sensation presenting device according to the embodiment of the present disclosure.

As illustrated in FIG. 6, the user holds the tactile sensation presenting device 300 as if holding a pen. Specifically, the user holds the tactile sensation presenting device 300 by placing their thumb to contact the casing 31 and the index finger on the contact unit 32. In this state, the index finger of the user is in contact with the contact unit 32 at a position 50. Therefore, at this position 50, the user can perceive the vibration of the tactile sensation presenting unit 330 as the tactile sensation via the contact unit 32.

Here a case of the user performing a medical operation by actually holding such a medical instrument as tweezers is considered. As illustrated in FIG. 7, the user holds the tweezers 400 as if holding a pen. In this state, the user positions the tweezers 400 between their thumb and index finger, and holds the tweezers 400 such that the rear end, which is the side of the tweezers 400 distant from the affected area, is placed on a vicinity of the base of the index finger (vicinity of a position of the finger corresponding to the proximal phalanx or metacarpal phalangeal joint (MP joint, third joint)). Thereby the user is in contact with the tweezers 400 at the position 60, the position 62 and the position 64. Hence when the user holds the tactile sensation presenting device 300, the user can perceive a tactile sensation that is closer to the actual tactile sensation, since the tactile sensation is presented at positions corresponding to the position 60, the position 62 and the position 64 of the tweezers 400. However, the tactile sensation presenting device 300 according to the comparative example has the tactile sensation presenting unit 330 only in the vicinity of the position 50, which corresponds to the position 60 of the tweezers 400. This means that the tactile sensation presenting device 300 cannot present the tactile sensations at the positions corresponding to the position 62 and the position 64 of the tweezers 400.

The tactile sensation presenting device 100 according to the present embodiment, on the other hand, includes the tactile sensation presenting units 130a, 130b and 130c, which are disposed in the vicinity of the position 70, the position 72 and the position 74 indicated in FIG. 8, as described with reference to FIG. 4. The position 70, the position 72 and the position 74 indicated in FIG. 8 are positions which are different from one another. Therefore, the tactile sensation presenting device 100 can present the tactile sensation to a plurality of different regions of the user. Furthermore, the position 70, the position 72 and the position 74 have a positional relationship corresponding to the positional relationship of the position 60, the position 62 and the position 64 indicated in FIG. 7 respectively. Therefore, at the position 70, the position 72 and the position 74, the tactile sensation presenting device 100 can present the user of the tactile sensation presenting units 130a, 130b and 130c respectively the tactile sensation that is closer to the tactile sensation perceived when the user performs a medical operation with actually holding the tweezers.

While an example of the tactile sensation presenting device 100 illustrated in FIG. 4 and FIG. 8 including three tactile sensation presenting units 130 was described above, it is sufficient if the tactile sensation presenting device 100 according to the present embodiment includes at least two tactile sensation presenting units 130. A first tactile sensation presenting unit 130, which is one of at least two tactile sensation presenting units 130, is disposed in the vicinity of a first position. A second tactile sensation presenting unit 130, which is the other of at least two tactile sensation presenting units 130, is disposed in the vicinity of a second position, which is different from the first position. For example, the first position is a position where the finger tip of the user comes into contact with the tactile sensation presenting device 100, and the second position is a position where the vicinity of the base of the finger of the user comes into contact with the tactile sensation presenting device 100. Specifically, the first position is the position 70, the first tactile sensation presenting unit 130 is the tactile sensation presenting unit 130a, the second position is the position 74, and the second tactile sensation presenting unit 130 is the tactile sensation presenting unit 130c. The first position may be the position 72, the first tactile sensation presenting unit 130 may be the tactile sensation presenting unit 130b, the second position may be the position 74, and the second tactile sensation presenting unit 130 may be the tactile sensation presenting unit 130c.

Further, for example, the first position may be a position where the finger tip of the user comes into contact with the tactile sensation presenting device 100, and the second position may also be a position where the finger tip of the user comes into contact with the tactile sensation presenting device 100. Specifically, the first position may be the position 70, the first tactile sensation presenting unit 130 may be the tactile sensation presenting unit 130a, the second position may be the position 72, and the second tactile sensation presenting unit 130 may be the tactile sensation presenting unit 130b.

The tactile sensation presenting unit 130 may be disposed at two positions confronting each other, where each base of the different fingers of the user comes into contact. For example, the first tactile sensation presenting unit 130 is disposed at a first position which is the position 74 on the casing 11 on the side of the base of the index finger. The second tactile sensation presenting unit 130 is disposed in a second position which is the position 72 in the casing 11 on the side of the base of the thumb, and which faces the first position.

As mentioned above, the tactile sensation presenting device 100 includes at least two tactile sensation presenting units 130 at different positions, whereby the tactile sensation can be presented to the user at a plurality of different regions, and a tactile sensation that is closer to the tactile sensation perceived when the user actually holds a medical instrument can be presented.

(Generation of Control Information)

In the master-slave system 1000, the master device 10 can present the tactile sensation to the user as vibration in accordance with the information related to the contact measured by the slave device 20. Specifically, the information related to the contact measured by the slave device 20 is sent to the master device 10. The master device 10 which received the information related to the contact generates control information which is used for driving the tactile sensation presenting unit 130, based on the received information related to the contact. Then based on the generated control information, the master device 10 drives the tactile sensation presenting unit 130, and presents the tactile sensation to the user.

The information related to the contact and the control information include information on the frequency and the displacement amount respectively. In the following, the frequency and the displacement amount included in the information related to the contact are also referred to as the first frequency and the first displacement amount respectively. Further, in the following, the frequency and the displacement amount included in the control information are also referred to as the second frequency and the second displacement amount respectively. The tactile sensation presenting unit 130 drives and generates vibration, so that the second displacement amount included in the inputted control information is implemented, and drives so that the frequency of this vibration becomes the second frequency.

However, in a common master-slave system, the above mentioned perceptual characteristic of a human is not considered. Therefore in some cases, the user may have difficulty or be unable to perceive the presented tactile sensation. For example, a master device of a common master-slave system acquires information related to the contact detected by the slave device, and presents the tactile sensation based on this acquired information related to the contact without performing any special signal processing. In this case, if the displacement amount of the tactile sensation presented to the user does not exceed the detection threshold in the graph in FIG. 5, the user has difficulty or is unable to perceive the tactile sensation presented as vibration by the tactile sensation presenting unit 130. Hence it is preferable that the second displacement amount included in the control information exceeds the detection threshold.

Hence the tactile sensation presenting device 100 according to the embodiment of the present disclosure generates the control information considering the perceptual characteristic of a human. As a result, the tactile sensation presenting device 100 can present a tactile sensation that the user can perceive more easily. The control information generation processing considering the perception of a human will be described in detail later.

<2-2-2. Functional Configuration Example of Tactile Sensation Presenting Device>

Figure 9:
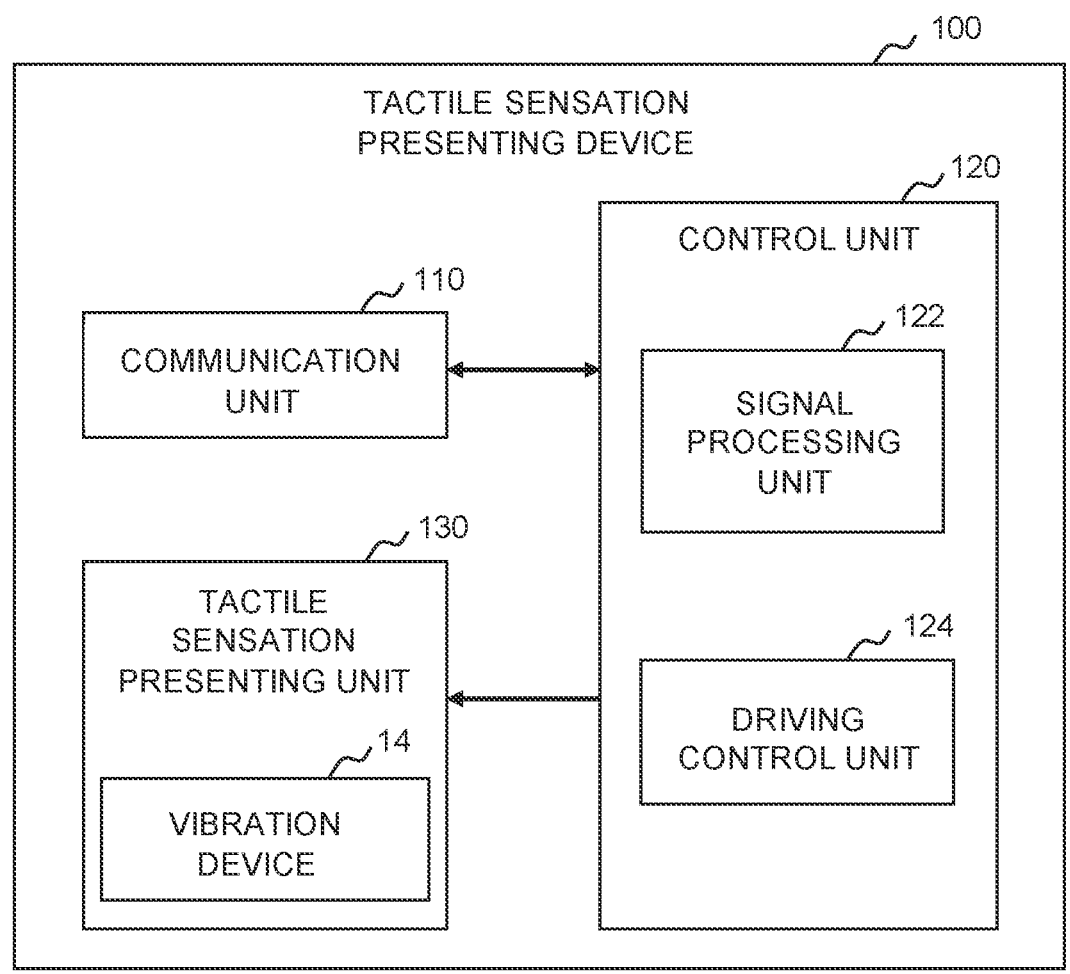
FIG. 9 is a block diagram depicting a functional configuration example of the tactile sensation presenting device according to the embodiment.

A functional configuration example of the tactile sensation presenting device 100 according to the embodiment of the present disclosure will be described with reference to FIG. 9. FIG. 9 is a block diagram depicting the functional configuration example of the tactile sensation presenting device according to the embodiment of the present disclosure. As illustrated in FIG. 9, the tactile sensation presenting device 100 includes a communication unit 110, a control unit 120 and the tactile sensation presenting unit 130.

(1) Communication Unit 110

The communication unit 110 has a function to communicate with another device. For example, in the communication with another device, the communication unit 110 outputs information received from the other device to the control unit 120. Specifically, the communication unit 110 outputs information related to the contact, which is received from the slave device 20, to the control unit 120.

Furthermore, in the communication with another device, the communication unit 110 sends information inputted from the control unit 120 to the other device. Specifically, the communication unit 110 sends information to instruct to operate the arm of the slave device 20, which is inputted from the control unit 120, to the slave device 20.

(2) Control Unit 120

The control unit 120 has a function to control operation of the master device 10. To implement this function, the control unit 120 according to the present embodiment includes a signal processing unit 122 and a driving control unit 124, as indicated in FIG. 9.

(2-1) Signal Processing Unit 122

The signal processing unit 122 has a function to process signals related to the operation of the master device 10 based on a signal inputted from the communication unit 110. For example, the signal processing unit 122 generates control information, which is different for each of the plurality of tactile sensation presenting units 130, based on the information related to the contact inputted from the communication unit 110, and provides the generated control information to each of the plurality of tactile sensation presenting units 130. The control information is information used for driving each of the plurality of tactile sensation presenting units 130. It should be noted that, as mentioned above, the information related to the contact includes the first frequency and the first displacement amount. Further, the control information includes the second frequency and the second displacement amount. Based on the first frequency and the first displacement amount, the signal processing unit 122 generates the control information so that at least one of the second frequency and the second displacement amount is different from the first frequency or the second displacement amount.

For example, the signal processing unit 122 generates the control information so that the second frequency is different from the first frequency. Specifically, the signal processing unit 122 generates a plurality of control information so that at least one second frequency, out of each second frequency of the plurality of control information, is higher than a predetermined threshold. More specifically, the signal processing unit 122 generates the control information so that the frequency, included in the control information provided to the tactile sensation presenting unit 130 which comes into contact with the vicinity of the finger tip of the user (vicinity of a position corresponding to a distal phalanx or a distal interphalangeal (DIP) joint, first joint), is higher than the predetermined threshold. The predetermined threshold may be set to 30 Hz, for example. If the frequency is higher than 30 Hz, the user can more easily perceive the vibration as a tactile sensation.

Further, the signal processing unit 122 generates a plurality of control information so that at least one second frequency, out of each second frequency of the plurality of control information, is lower than a predetermined threshold. More specifically, the signal processing unit 122 generates the control information so that the frequency, included in the control information provided to the tactile sensation presenting unit 130 which comes into contact with the vicinity of the base of the finger of the user, is lower than the predetermined threshold. The predetermined threshold may be set to 30 Hz, for example.

Further, the signal processing unit 122 generates the control information so that at least one second frequency, out of each second frequency of the plurality of control information, is higher than a predetermined threshold, and at least one second frequency thereof is lower than the predetermined threshold. Thereby different tactile sensations are presented by at least two tactile sensation presenting units 130. This allows the user to detect different tactile sensations in at least two regions, and makes it easier for the user to perceive the tactile sensations.

In the case where the user performs a medical operation by actually holding a medical instrument, such as tweezers, the vibration generated by the contact between the medical instrument and the patient propagates through the medical instrument and is transferred to the user. In this case, the vibration that transfers through the medical instrument attenuates while propagating from the far end side, which is the front end side of the medical instrument distant from the hand of the user, to the near end side, which is the rear end side of the medical instrument close to the hand of the user. Therefore on the far end side of the medical instrument, vibration, which is stronger than the vibration transferred to the user on the near end side of the medical instrument, is transferred to the user. Hence the signal processing unit 122 provides the control information, which includes the second frequency that is higher than a predetermined threshold, to the tactile sensation presenting unit 130 disposed in a position where the vicinity of the finger tip of the user comes into contact. The signal processing unit 122 also provides the control information, which includes the second frequency that is lower than the predetermined threshold, to the tactile sensation presenting unit 130 disposed in a position where the vicinity of the base of the finger of the user comes into contact. Thereby the signal processing unit 122 can present to the user a tactile sensation that is closer to the tactile sensation which the user perceives when the user performs a medical operation with actually holding a medical instrument, such as a tweezers.

Further, the signal processing unit 122 may generate the plurality of control information so that the plurality of control information includes the second frequency within a predetermined range. For example, for the predetermined range, a frequency band, in which the vibration device used for the tactile sensation presenting unit 130 can present the vibration as the tactile sensation, is set. Specifically, in the case where VCM is used for the vibration device, 30 Hz to 700 Hz may be set for the predetermined range. Thereby the tactile sensation presenting device 100 can present a tactile sensation in accordance with the performance of the vibration device that is used for the tactile sensation presenting unit 130. Further, the signal processing unit 122 may generate the control information so that the frequency of the vibration of the tactile sensation to be presented is constant. Using this control information, the tactile sensation presenting unit 130 can present the user a vibration having a constant frequency, as the tactile sensation. For example, if the vibration of which frequency fluctuates is presented as the tactile sensation by the tactile sensation presenting unit 130 when the user is performing a precise operation, the presented vibration of the tactile sensation may affect the operation by the user. By presenting a vibration having a constant frequency as the tactile sensation, influence on the operation by the user can be minimized.

Further, the signal processing unit 122 may generate the control information in accordance with the perceptual characteristic of a region where each of the plurality of tactile sensation presenting units 130 comes into contact. The region where each of the plurality of tactile sensation presenting units 130 comes into contact refers to a region where each of the plurality of tactile sensation presenting units 130 comes into contact with the hand of the user when the user holds the tactile sensation presenting device 100 by hand. For example, the signal processing unit 122 generates the control information so that the second frequency and the second displacement amount correspond to the frequency and the displacement amount which are detectable by the tactile receptors in the region where each of the plurality of tactile sensation presenting units 130 comes into contact. Specifically, the signal processing unit 122 generates the control information so that the second frequency and the second displacement amount exceed the detection threshold of the tactile receptors in the region where each of the plurality of tactile sensation presenting units 130 comes into contact.

As an example of generating this control information, the signal processing unit 122 may generate the control information so that the second frequency is different from the first frequency, and the second displacement amount is the same as the first displacement amount. For example, in the case where the first frequency is 1 Hz and the first displacement amount is about 4 μm, the Pacinian corpuscles detect vibration if the frequency is about 100 Hz. Therefore the signal processing unit 122 generates the control information so that the second frequency becomes about 100 Hz and the second displacement amount becomes about 4 μm. Then the tactile sensation presenting unit 130 can present the tactile sensation which the user can easily perceive, even if the displacement amount measured on the slave device 20 side is small.

Further, the signal processing unit 122 may generate the control information so that the second frequency is the same as the first frequency, and the second displacement amount is different from the first displacement amount. More specifically, in the case where the first frequency is 1 Hz and the first displacement amount is about 4 μm, the Merkel corpuscles detect the vibration if the displacement amount is at least about 100 μm. Therefore the signal processing unit 122 generates the control information so that the second frequency becomes about 1 Hz, and the second displacement amount becomes at least about 100 μm. Then the tactile sensation presenting unit 130 can present the tactile sensation which the user can easily perceive, even if the frequency measured on the slave device 20 side is small.

Further, the signal processing unit 122 may generate the control information so that both the second frequency and the second displacement amount are different from the first frequency and the first displacement amount respectively. More specifically, in the case where the first frequency is 1 Hz and the first displacement amount is about 4 μm, the Meissner corpuscles detect the vibration if the frequency is about 10 Hz and the displacement amount is at least about 40 μm. Therefore the signal processing unit 122 generates the control information so that the second frequency becomes about 10 Hz, and the second displacement amount becomes at least about 40 μm. Then the tactile sensation presenting unit 130 can present the tactile sensation which the user can easily perceive, even if the frequency and the displacement amount measured on the slave device 20 side are small. Also the range of the tactile sensation which the user can easily perceive can be expanded.

Further, the signal processing unit 122 may generate the control information so that the frequencies included in the entire control information provided to the plurality of tactile sensation presenting units 130 are frequencies exceeding the detection threshold of the tactile receptors. The signal processing unit 122 can expand the range where the user can perceive the vibration by increasing the second frequency so as to exceed the detection threshold of the tactile receptors, even if the vibration corresponding to the information related to the contact measured on the slave device 20 side is a minute vibration.

As described above, by the signal processing unit 122 generating the control information with considering the perceptual characteristic of users in each region where each of the plurality of the tactile sensation presenting units 130 comes into contact, the user can more easily perceive the tactile sensation generated by the vibration presented by each tactile sensation presenting unit 130.

In some cases, the perceptual characteristic of a human may be different depending on the user. For example, the perceptual characteristic may be different depending on age, gender, skin condition, and the like of the user. Hence the signal processing unit 122 may generate the control information in accordance with the perceptual characteristic of each user. Then the tactile sensation presenting device can present to each user the tactile sensation in accordance with the perceptual character of the user. The user can more easily perceive the tactile sensation since tactile sensation in accordance with their own perceptual characteristic is presented.

Figure 10:
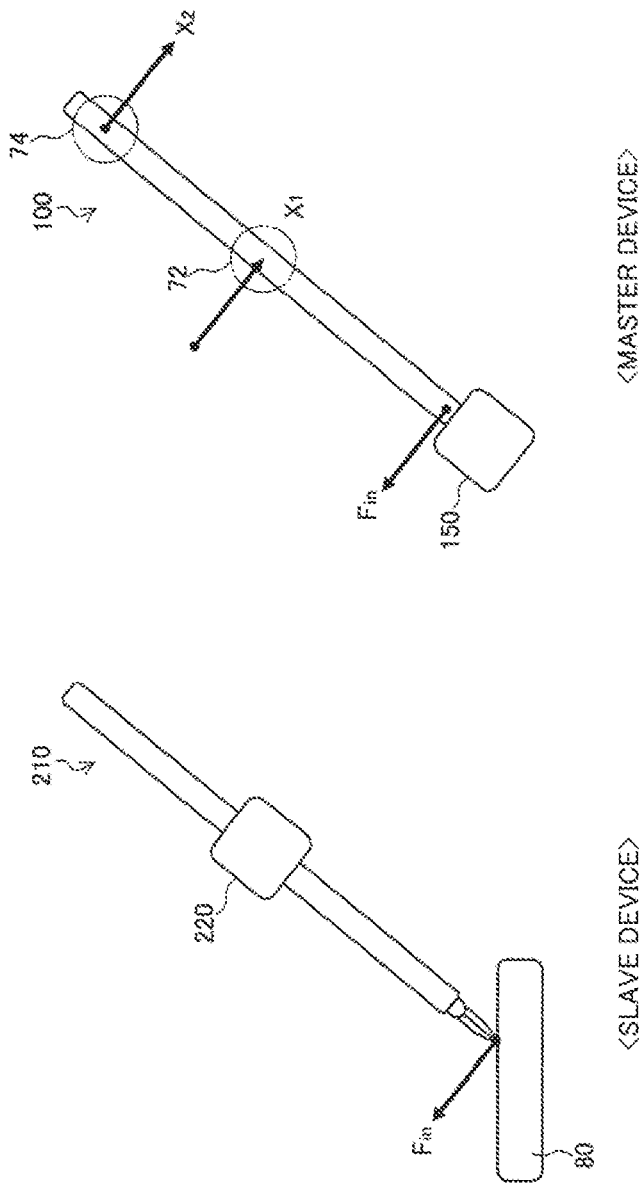
FIG. 10 is an explanatory drawing of an example of forces related to the master device and the slave device according to the embodiment.

A specific method of calculating the second displacement amount will now be described with reference to FIG. 10. FIG. 10 is an explanatory drawing of an example of forces related to the master device and the slave device according to the embodiment of the present disclosure.

As illustrated in the drawing on the left side of FIG. 10, it is assumed that the force $F_{in}$ is applied to the front end of the operation tool 210 when the operation tool 210 of the slave device 20 comes into contact with an affected area 80 of a patient. This $F_{in}$ is measured by a force sensor 220. As illustrated in the drawing on the right side of FIG. 10, it is assumed that this $F_{in}$ is applied to the vicinity of the force sensor 150 in the master device 10. The second displacement amount corresponding to this force $F_{in}$ is calculated by amplifying $F_{in}$ by a magnification $k_G$. For example, the second displacement amount X is calculated by $X=k_G \times F_{in}$. The magnification $k_G$ may be adjusted in accordance with the position of the tactile sensation presenting unit 130 for which the second displacement amount is calculated. By adjusting the magnification $k_G$, the signal processing unit 122 can calculate a different displacement amount for the displacement amount $X_1$ at the position 72 and the displacement amount $X_2$ at the position 74. It is preferable that the second displacement amount X is larger than the detection threshold.

(2-2) Driving Control Unit 124

The driving control unit 124 has a function to control driving of the tactile sensation presenting unit 130 based on the signal inputted from the signal processing unit 122. For example, the driving control unit 124 controls driving of the tactile sensation presenting unit 130 based on the control information inputted from the signal processing unit 122. Specifically, the driving control unit 124 generates instruction information related to driving of the tactile sensation presenting unit 130 based on the control information. Then the driving control unit 124 outputs the generated instruction information to the tactile sensation presenting unit 130.

(3) Tactile Sensation Presenting Unit 130

The tactile sensation presenting unit 130 has a function to present the tactile sensation to the user. For example, the tactile sensation presenting unit 130 presents the tactile sensation to the user by vibration. Specifically, the tactile sensation presenting unit 130 includes a vibration device 14, and transfer the vibration, which is generated by driving the vibration device 14, to the user. By perceiving this vibration via the tactile sensation presenting unit 130, the user can perceive a pseudo-tactile sensation.

The tactile sensation presenting unit 130 drives the vibration device 14 based on the instruction information inputted from the driving control unit 124. For example, the instruction information inputted from the driving control unit 124 includes such instructions as the vibration frequency, the displacement amount and the vibration direction when the vibration device 14 vibrates. The tactile sensation presenting unit 130 drives the vibration device 14 in accordance with the instruction information.

The vibration device 14 may be an arbitrary vibration device, such as a voice coil motor type vibration actuator, an LRA, and a piezoelectric element. The vibration device 14 may be a vibration device which can vibrate in an arbitrary direction. For example, the vibration device 14 may be a device which can vibrate in three axis directions, or may be a device which can vibrate in only one axis direction.

3. Modifications

The modifications of the embodiment of the present disclosure will now be described. The modifications described below may be applied to the embodiment of the present disclosure by itself, or may be applied to the embodiment of the present disclosure as a combination. The modifications may be applied instead of the configuration described in the embodiment of the present disclosure, or may be applied additionally to the configuration described in the embodiment of the present disclosure.

3-1. Modification 1

Figure 11:
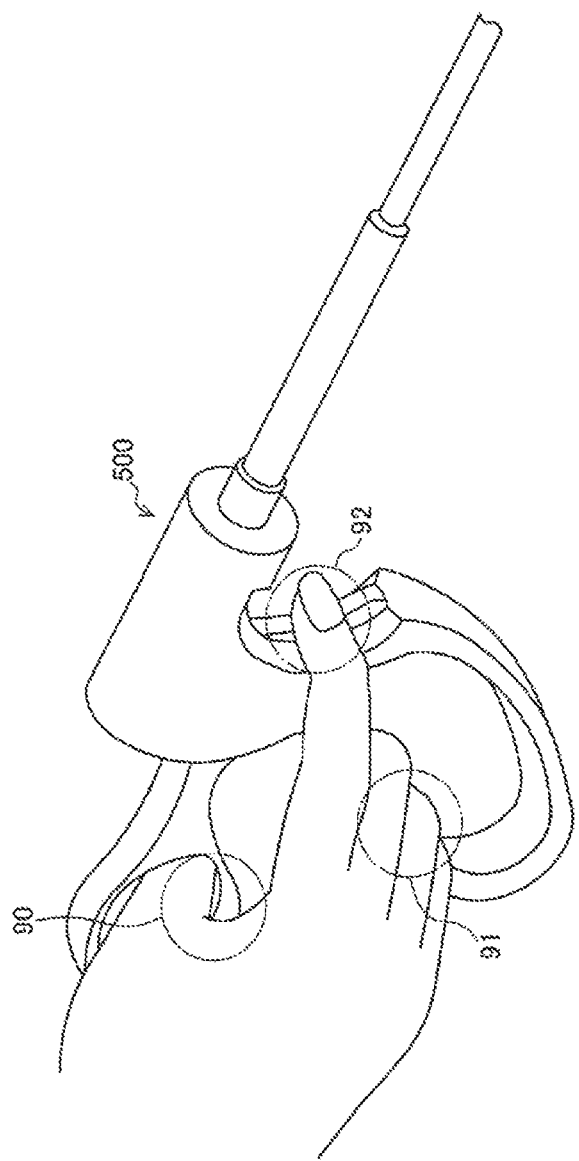
FIG. 11 is an explanatory drawing of Modification 1 according to the embodiment.

Modification 1 according to the embodiment of the present disclosure will now be described with reference to FIG. 11. FIG. 11 is an explanatory drawing of Modification 1 according to the embodiment of the present disclosure.

The position where the tactile sensation presenting unit 130 is disposed may be different depending on the shape of the tactile sensation presenting device. For example, an example of a tactile sensation presenting device 500 having a needle holder shape, which is held as if holding scissors, will be described. It is preferable that the tactile sensation presenting device 500 also includes at least two tactile sensation presenting units 130 at different positions. For example, the tactile sensation presenting unit 130 is disposed in at least two positions: a first position, which is a position where the finger tip of the user comes into contact with the tactile sensation presenting device 500; and a second position, which is a position where the base of the finger of the user comes into contact with the tactile sensation presenting device 500. Specifically, the first position is the position 92 and the second position is the position 90. However, the first position may be the position 92 and the second position may be the position 91. It should be noted that the tactile sensation presenting unit 130 may be disposed in all the positions of the position 90, the position 91 and the position 92.

The tactile sensation presenting device 500 includes at least two tactile sensation presenting units 130 at different positions, whereby the tactile sensation can be presented to the user at a plurality of different regions, and a tactile sensation that is closer to the tactile sensation perceived when the user actually holds the medical instrument can be presented.

3-2. Modification 2

Figure 12:
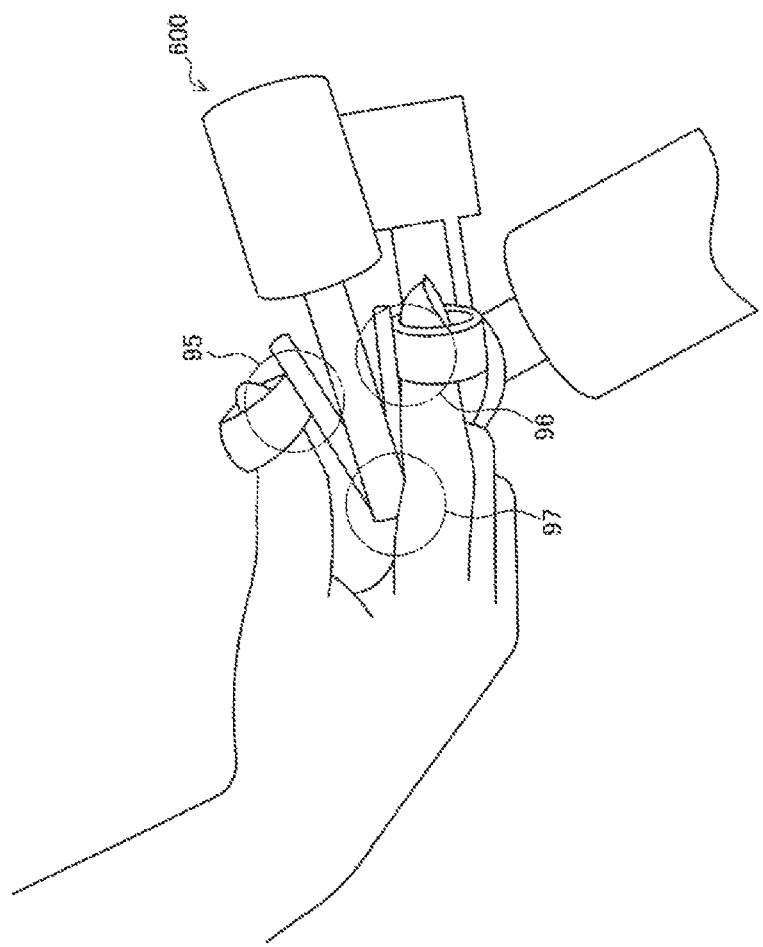
FIG. 12 is an explanatory drawing of Modification 2 according to the embodiment.

Modification 2 according to the embodiment of the present disclosure will now be described with reference to FIG. 12. FIG. 12 is an explanatory drawing of Modification 2 according to the embodiment of the present disclosure.

The position where the tactile sensation presenting unit 130 is disposed may be different depending on the shape of the tactile sensation presenting device. For example, an example of a tactile sensation presenting device 600, having a shape that is held between the fingertips of two fingers, will be described. It is preferable that the tactile sensation presenting device 600 as well includes at least two tactile sensation presenting units 130 disposed in at different positions. For example, the tactile sensation presenting unit 130 is disposed in at least two positions: a first position, which is a position where the finger tip of the user comes into contact with the tactile sensation presenting device 600; and a second position, which is a position where the base of the finger of the user comes into contact with the tactile sensation presenting device 600. Specifically, the first position is the position 95 and the second position is the position 97. However, the first position may be the position 96 and the second position is the position 97. It should be noted that the tactile sensation presenting unit 130 may be disposed at all the positions of the position 95, the position 96 and the position 97.

The tactile sensation presenting device 600 includes at least two tactile sensation presenting units 130 at different positions, whereby the tactile sensation can be presented to the user at a plurality of different regions, and a tactile sensation that is closer to the tactile sensation perceived when the user actually holds the medical instrument can be presented.

3-3. Modification 3

Figure 13:
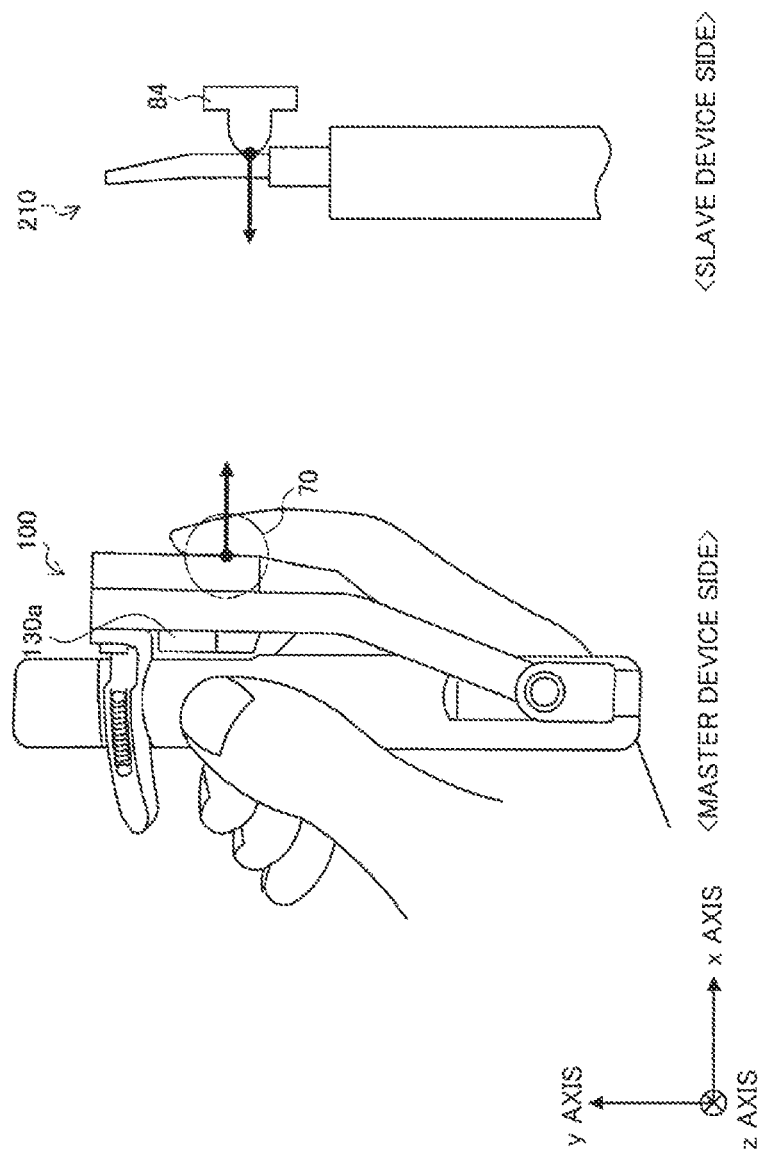
FIG. 13 is an explanatory drawing of Modification 3 according to the embodiment.
Figure 14:
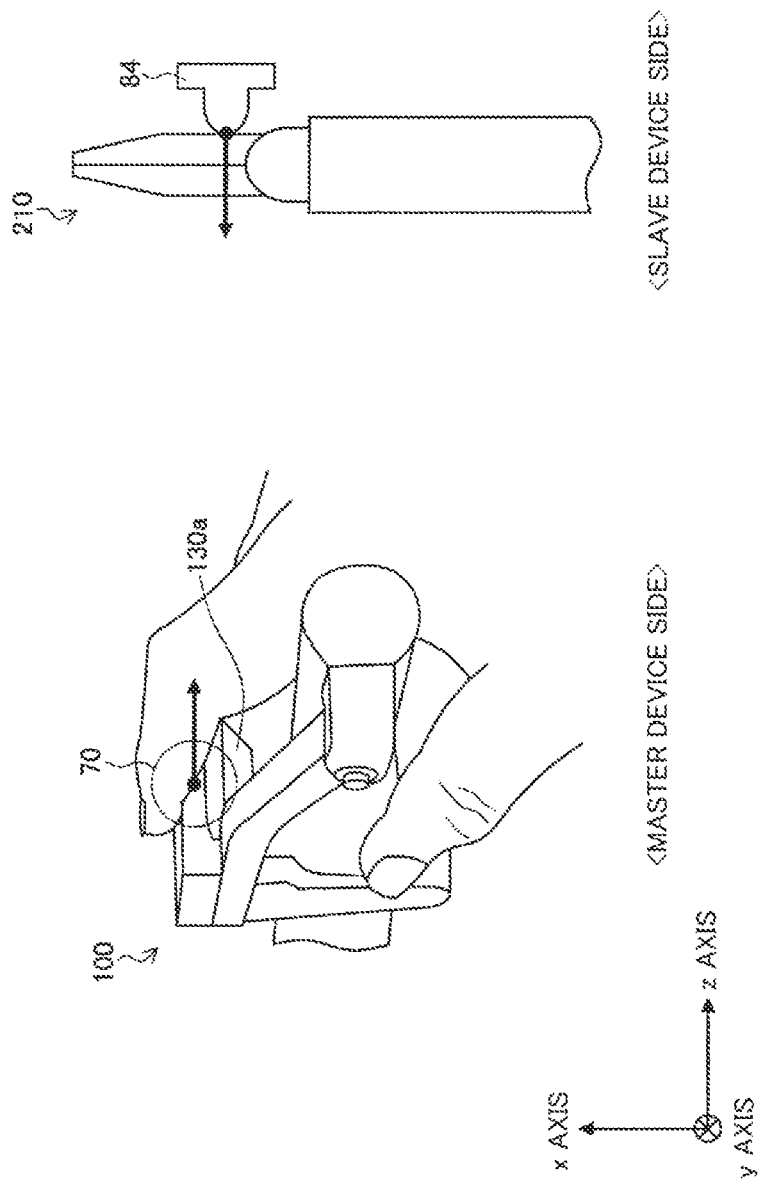
FIG. 14 is an explanatory drawing of Modification 3 according to the embodiment.
Figure 15:
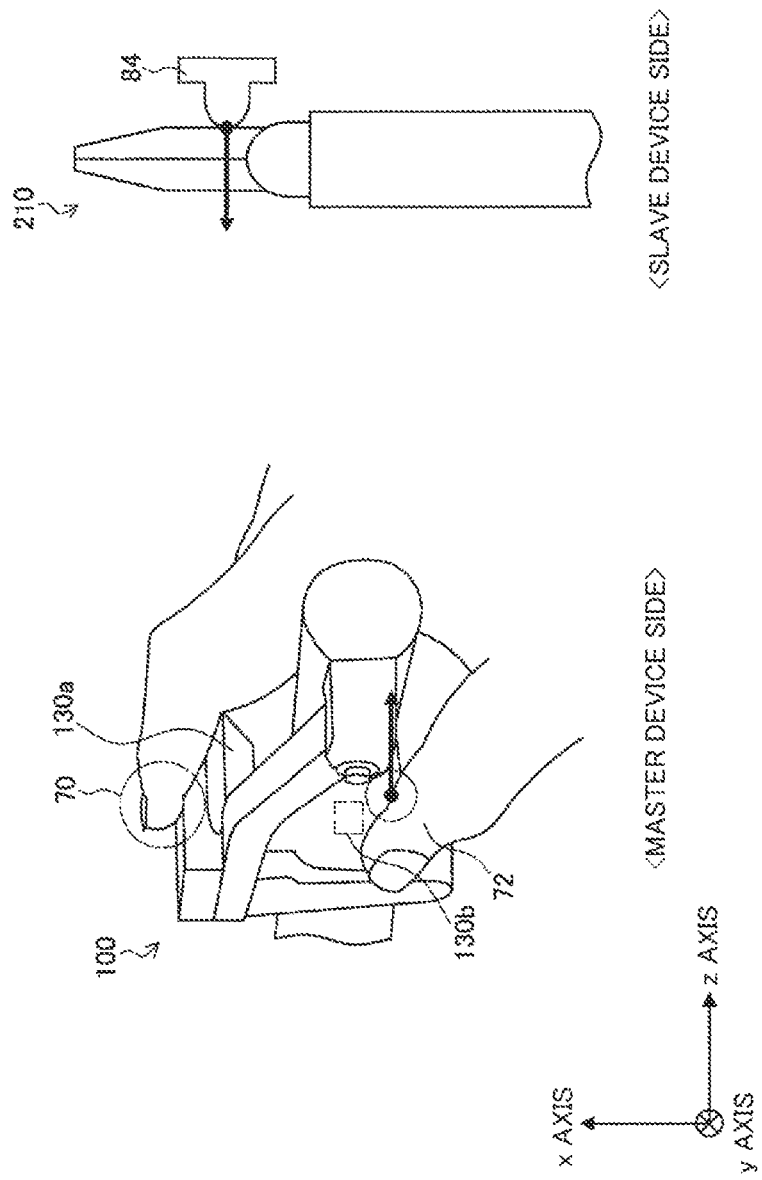
FIG. 15 is an explanatory drawing of Modification 3 according to the embodiment.

Modification 3 according to the embodiment of the present disclosure will now be described with reference to FIG. 13 to FIG. 15. FIG. 13 to FIG. 15 are explanatory drawings of Modification 3 according to the embodiment of the present disclosure. FIG. 13 is an example of presenting the tactile sensation in the positive direction of the x axis by the tactile sensation presenting unit 130*a* which can vibrate in the three axis directions. FIG. 14 is an example of presenting the tactile sensation in the positive direction of the z axis by the tactile sensation presenting unit 130*a* which can vibrate in the three axis directions. FIG. 15 is an example of presenting the tactile sensation in the positive direction of the z axis by the tactile sensation presenting unit 130*b* which can vibrate in one axis direction. It is assumed that the x axis, the y axis and the z axis illustrated in each drawing of FIG. 13 to FIG. 15 indicate the positive directions respectively.

The information related to the contact and the control information further include direction information related to the direction corresponding to the direction of the contact force generated when the operation tool 210 comes into contact with the object, and the plurality of tactile sensation presenting units 130 may present the tactile sensation in the direction indicated by this direction information. For example, as the direction information, the information related to the contact includes the measurement data generated by the force sensor 220 of the operation tool 210. The signal processing unit 122, to which this information related to the contact is inputted, acquires the direction of the contact force based on the measurement data generated by the force sensor 220. Then the signal processing unit 122 includes the direction information, which indicates the direction corresponding to the acquired direction of the contact force, in the control information, and outputs this control information to the tactile sensation presenting unit 130. Thereby the tactile sensation presenting unit 130, to which the control information is inputted, vibrates in the direction indicated by the direction information.

A specific example of the direction of the tactile sensation presented by the tactile sensation presenting unit 130 will be described. First a case where the vibration device used for the tactile sensation presenting unit 130 can vibrate in the three axis directions will be described with reference to FIG. 13 and FIG. 14. As illustrated in the drawing on the right side of FIG. 13, it is assumed that when the front end of the operation tool 210 of the slave device 20 comes into contact with the object 84, the contact force is generated in the operation tool 210 in the negative direction of the x axis. In this case, as illustrated in the drawing on the left side of FIG. 13, the tactile sensation presenting unit 130 vibrates in the positive direction of the x axis, whereby the tactile sensation is presented at the position 70 in the direction corresponding to the contact force. Further, as illustrated in the drawing on the right side of FIG. 14, it is assumed that when the front end of the operation tool 210 of the slave device 20 comes into contact with the object 84, the contact force is generated in the operation tool 210 in the negative direction of the z axis. In this case, as illustrated in the drawing on the left side of FIG. 14, the tactile sensation presenting unit 130 vibrates in the positive direction of the z axis, whereby the tactile sensation is presented at the position 70 in the direction corresponding to the contact force.

Next, a case where the vibration device used for the tactile sensation presenting unit 130 can vibrate in the one axis direction will be described with reference to FIG. 15. As illustrated in the drawing on the left side of FIG. 15, it is assumed that the tactile sensation presenting unit 130*a* can vibrate in the x axis direction, and the tactile sensation presenting unit 130*b* can vibrate in the z axis direction. For example, as illustrated in the drawing on the right side of FIG. 15, it is assumed that when the front end of the operation tool 210 of the slave device 20 comes into contact with the object 84, the contact force is generated in the operation tool 210 in the negative direction of the z axis. At this time, the direction of the tactile sensation corresponding to the contact force in the negative direction of the z axis is assumed to be the position direction of the z axis. In this case, the tactile sensation presenting unit 130*a*, which vibrates in the x axis direction, cannot present this tactile sensation, but the tactile sensation presenting unit 130*b*, which vibrates in the z axis direction, can present this tactile sensation. Therefore, as illustrated in the drawing on the left side of the FIG. 15, the tactile sensation presenting unit 130*b* vibrates in the position direction of the z axis, whereby the tactile sensation is presented at the position 72 in a direction corresponding to the contact force.

As described above, the tactile sensation presenting unit 130 can present the tactile sensation in a direction corresponding to the direction of the contact force generated when the operation tool 210 comes into contact with the object. Thereby the user can perceive a tactile sensation that is closer to the tactile sensation perceived when the user actually holds the medical instrument.

3-4. Modification 4

Modification 4 according to the embodiment of the present disclosure will now be described.

The tactile sensation presenting device 100 may further include an acceleration sensor. Thereby the signal processing unit 122 may generate the control information in accordance with the acceleration measured by the acceleration sensor. For example, in the case where the tactile sensation presenting unit 130 presents vibration, of which frequency and displacement amount are small, to the user as the tactile sensation when the user is making a big movement with operating the tactile sensation presenting device 100 during operation, the user may have difficulty in perceiving the tactile sensation. Furthermore, if the tactile sensation presenting unit 130 presents a vibration, of which frequency and displacement are large, to the user as the tactile sensation when the user is performing a precise operation, the operation of the user may be affected.

Hence the acceleration sensor measures the acceleration that is generated when the user operates the tactile sensation presenting device 100. Then the signal processing unit 122 generates the control information in accordance with the acceleration measured by the acceleration sensor. For example, in the case where the measured acceleration is large, the user may be making a big movement with the tactile sensation presenting device 100 during operation, therefore the signal processing unit 122 generates the control information of which frequency and displacement amount are large. Then the tactile sensation presenting unit 130 can present tactile sensation which can be easily perceived even if the user is making a big movement with the tactile sensation presenting device 100 during operation. In the case where the measured acceleration is small, on the other hand, the user may be performing a precise operation, therefore the signal processing unit 122 generates the control information of which frequency and displacement amount are small. Then the tactile sensation presenting unit 130 can present tactile sensation which has little effect on the precise operation that is being performed by the user.

As described above, the signal processing unit 122 generates control information in accordance with the acceleration, whereby the tactile sensation presenting unit 130 can present the user the tactile sensation in accordance with the operating state of the tactile sensation presenting device 100 by the user.

3-5. Modification 5

Modification 5 according to the embodiment of the present disclosure will now be described.

The region in contact with the tactile sensation presenting device 100 is not always a region which has a perceptual characteristic that can perceive the tactile sensation most easily in the body of the user. Therefore a tactile sensation presenting unit, which is different from the plurality of tactile sensation presenting units 130 included in the tactile sensation presenting device 100, may additionally be disposed outside the tactile sensation presenting device 100. By this different tactile sensation presenting unit, the user can perceive the tactile sensation at a region other than their hand holding the tactile sensation presenting device 100. This different tactile sensation presenting unit may be disposed in such an external device as a wearable device, for example. By wearing this wearable device around the wrist, for example, the user can perceive the tactile sensation on their wrist. Further, the different tactile sensation presenting unit may be disposed in such an external device as a glove type device. The glove type device comes into contact with a plurality of regions of the user. Therefore in the glove type device, a different tactile sensation presenting unit can be disposed at each position that comes into contact with each of a plurality of regions of the user, whereby the tactile sensation can be presented to each of the plurality of regions of the user. The different tactile sensation presenting unit may be disposed so as to contact with a region having a perceptual characteristic which allows the user to perceive the tactile sensation more easily than the region where the tactile sensation presenting unit 130 comes into contact. Thereby the user can perceive the tactile sensation more easily. It should be noted that the signal processing unit 122 generates the control information in accordance with the perceptual characteristic of the region where this different tactile sensation presenting unit comes into contact, and provides the control information to the different tactile sensation presenting unit.

As described above, by disposing a different tactile sensation presenting unit that comes into contact with a region having the perceptual characteristic which allows the user to perceive the tactile sensation more easily, the tactile sensation presenting device 100 can present the tactile sensation to a region where the user can perceive the tactile sensation more easily.

4. Hardware Configuration Example

Figure 16:
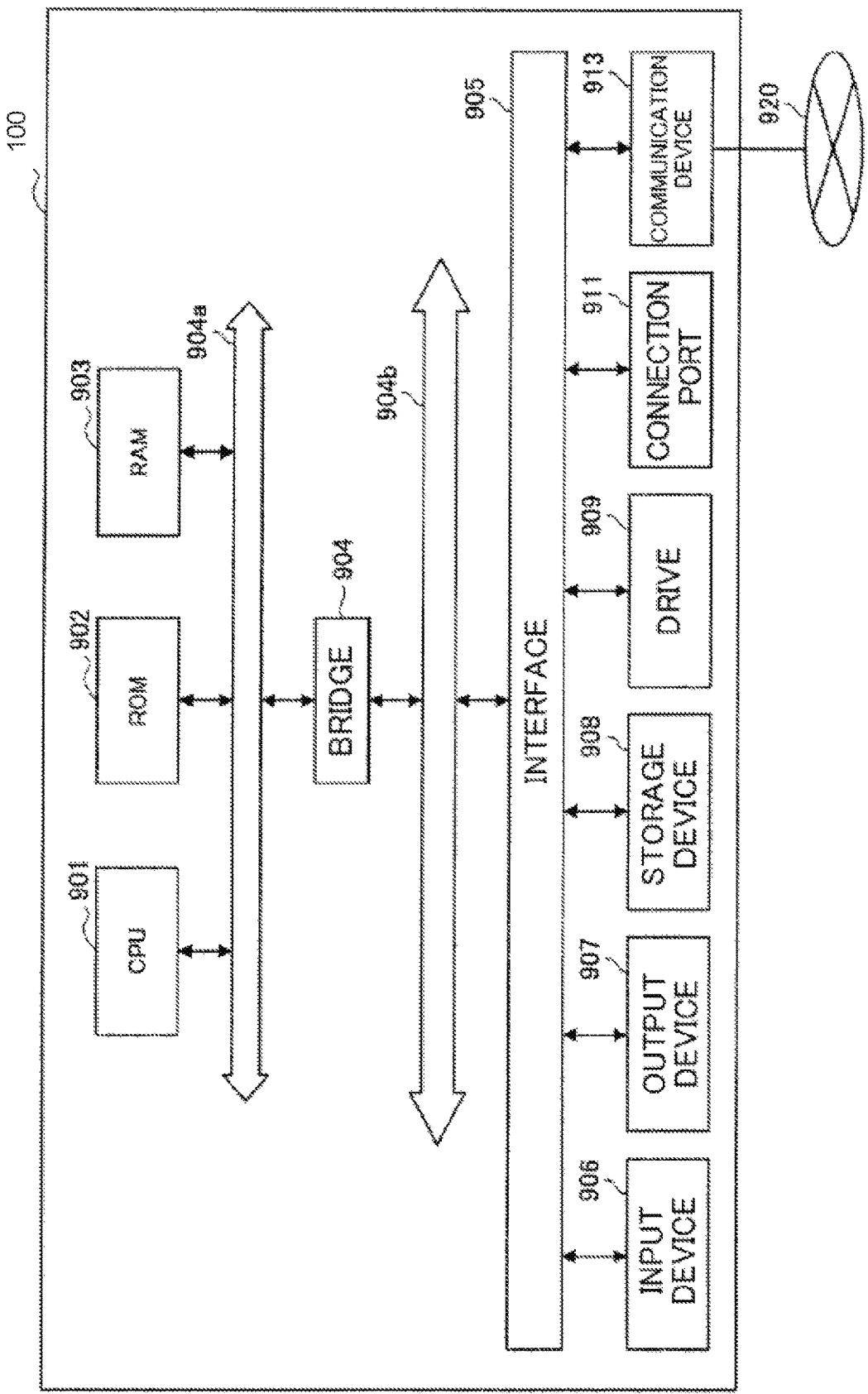
FIG. 16 is a block diagram depicting an example of a hardware configuration of the master device according to the embodiment.

The embodiment of the present disclosure was described above. Finally, a hardware configuration according to the embodiment of the present disclosure will be described with reference to FIG. 16. FIG. 16 is a block diagram depicting an example of the hardware configuration of the tactile sensation presenting device according to the embodiment of the present disclosure. The tactile sensation presenting device 100 indicated in FIG. 16 can implement the functions of the tactile sensation presenting device 100 indicated in FIG. 9. The image processing by the tactile sensation presenting device 100 according to the present embodiment is implemented by a combination of software and hardware which will be described below.

As indicated in FIG. 16, the tactile sensation presenting device 100 includes a central processing unit (CPU) 901, a read only memory (ROM) 902 and a random access memory (RAM) 903. The tactile sensation presenting device 100 also includes a host bus 904*a*, a bridge 904, an external bus 904*b*, an interface 905, an input device 906, an output device 907, a storage device 908, a drive 909, a connection port 911 and a communication device 913. This hardware configuration is an example, and a part of the composing elements may be omitted. The hardware configuration may further include composing elements other than the composing elements indicated here.

(CPU 901, ROM 902, RAM 903)

The CPU 901 functions as an arithmetic processing unit or a control device, and controls all or a part of the operation of the composing elements based on various programs recorded in the ROM 902, the RAM 903 or the storage device 908. The ROM 902 is a unit that stores programs to be read by the CPU 901, data used for operation, and the like. In the RAM 903, programs read by the CPU 901, various parameters which appropriately change when these programs are executed, and the like are temporarily or permanently stored. These units are interconnected via the host bus 904*a*, which is constituted of a CPU bus, for example. The CPU 901, the ROM 902 and the RAM 903 can implement the functions of the control unit 120 described with reference to FIG. 9, based on combination with software, for example.

(Host Bus 904*a*, Bridge 904, External Bus 904*b*, Interface 905)

The CPU 901, the ROM 902 and the RAM 903 are interconnected via the host bus 904*a*, for example, which can perform high-speed data transmission. The host bus 904*a* is also connected to the external bus 904*b*, of which data transmission speed is relatively slow, via the bridge 904, for example. The external bus 904*b* is connected with various composing elements via the interface 905.

(Input Device 906)

The input device 906 is implemented by a device with which the user inputs information, such as a mouse, a keyboard, a touch panel, a button, a microphone, a switch and a lever, for example. The input device 906 may be a remote control device using infrared or other radio waves, or may be an externally connected apparatus, such as a portable telephone and a PDA. Further, the input device 906 may include an input control circuit, which generates input signals using the above mentioned input units based on the information inputted by the user, and outputs the input signals to the CPU 901, for example. By operating this input device 906, the user of the tactile sensation presenting device 100 can input various data to or instruct the processing operation to the tactile sensation presenting device 100.

Further, the input device 906 may be implemented by a device that detects information related to the user. For example, the input device 906 may include various sensors, such as an image sensor (e.g. camera), a depth sensor (e.g. stereo camera), an acceleration sensor, a gyro sensor, a geo-magnetic sensor, a photo sensor, a sound sensor, a distance measuring sensor (e.g. Time of Flight (ToF) sensor), and a force sensor. Furthermore, the input device 906 may acquire information related to the state of the tactile sensation presenting device 100, such as an attitude and moving speed of the tactile sensation presenting device 100, or information related to the surrounding environment of the tactile sensation presenting device 100, such as brightness and noise in the surroundings of the tactile sensation presenting device 100. The input device 906 may also include a global navigation satellite system (GNSS) module, that receives a GNSS signal from the GNSS satellite (e.g. a global positioning system (GPS) signal from the GPS satellite), and measures the position information on the device including latitude, longitude and altitude. For the position information, the input device 906 may detect the position via Wi-Fi® via communication using a portable telephone, PHS, smartphone or the like, or via short range communication.

(Output Device 907)

The output device 907 is constituted of a device which can notify the acquired information to the user visually or aurally. Such devices are: display devices, including a CRT display device, a liquid crystal display device, a plasma display device, an EL display device, a laser projector, an LED projector and a lamp; sound output devices, including a speaker and headphone; and printer devices. For example, the output device 907 outputs the result acquired by various types of processing which the tactile sensation presenting device 100 performed. Specifically, the display device visually displays the results acquired by various types of processing which the tactile sensation presenting device 100 performed, using various formats, such as text, images, tables and graphs. The sound output device, on the other hand, converts audio signals constituted of reproduced sound data, acoustic data or the like into analog signals, and outputs the analog signals aurally.

(Storage Device 908)

The storage device 908 is a data storage device which is structured as an example of the storage unit of the tactile sensation presenting device 100. The storage device 908 is implemented by, for example, a magnetic storage device, such as an HDD, a semiconductor storage device, an optical storage device, a magneto-optical storage device, or the like.

The storage device 908 may include: a storage medium; a recording device that records data on the storage medium; a reading device that reads data from the storage medium; a deleting device that deletes the data recorded in the storage medium; and the like. The storage device 908 stores programs and various data executed by the CPU 901, various externally acquired data, and the like.

(Drive 909)

The drive 909 is a storage medium reader/writer, and is enclosed in or externally attached to the tactile sensation presenting device 100. The drive 909 reads information recorded in the installed removable storage medium, such as a magnetic disk, an optical disk, a magneto-optical disk, a semiconductor memory or the like, and outputs the information to the RAM 903. The drive 909 can also write information in the removable storage medium.

(Connection Port 911)

The connection port 911 is a port to connect an external connection device, such as a universal serial bus (USB) port, an IEEE 1394 port, a small computer system interface (SCSI) port, an RS-232C port, an optical audio terminal, or the like.

(Communication Device 913)

The communication device 913 is a communication interface structured by a communication device to connect to the network 920, for example. The communication device 913 is a communication card for a cable or wireless local area network (LAN), a long term evolution (LTE), Bluetooth® or wireless USB (WUSB), for example. The communication device 913 may also be a router for optical communication, a router for an asymmetric digital subscriber line (ADSL), or a modem for various communications, for example. This communication device 913 can transmit/receive signals and the like to/from the Internet or other communication apparatuses, in accordance with a predetermined protocol, such as TCP/IP.

It should be noted that the network 920 is cable or wireless transmission lines for information transmitted from devices connected to the network 920. For example, the network 920 may include a public line network, such as the Internet, a telephone line network and a satellite communication network, and various types of local area networks (LAN) including Ethernet®, and wide area networks (WAN), for example. The network 930 may also include a leased line network, such as internet protocol-virtual private network (IP-VPN).

The hardware configuration example of the tactile sensation presenting device 100 according to the present embodiment has been described with reference to FIG. 16. Each composing element described above may be implemented by a general purpose member, or may be implemented by hardware specialized for providing functions of each composing element. In other words, the hardware configuration to be used may be changed in accordance with the specific technical level required to implement the present embodiment.

5. Conclusion

As described above, the tactile sensation presenting device 100 according to the embodiment of the present disclosure includes a plurality of tactile sensation presenting units 130 that presents the tactile sensation based on the control information. Further, the tactile sensation presenting device 100 generates the control information that is different for each of the plurality of tactile sensation presenting units 130 based on the information related to the contact between the operation tool 210 and the object, generated using the operation tool 210. Then the tactile sensation presenting device 100 provides the generated control information to each of the plurality of tactile sensation presenting units.

Because of the above mentioned configuration, the tactile sensation presenting device 100 can present the user with a different tactile sensation at each of the plurality of tactile sensation presenting units 130. Thereby the user can perceive a tactile sensation that is different for each region which is in contact with the tactile sensation presenting unit 130. In the case where the user actually holds a medical instrument and performs the medical operation, the user normally perceives tactile sensation that is different depending on the contact position, hence the user can perceive a tactile sensation that is closer to the tactile sensation perceived when the medical operation is performed with actually holding the medical instrument.

As a consequence, a new and improved tactile sensation presenting device and tactile sensation presenting system, which are capable of presenting a tactile sensation that the user can perceive more easily, can be provided.

While the preferred embodiments of the present disclosure have been described in detail with reference to the accompanying drawings, the technical scope of the present disclosure is not limited to these examples. It should be understood that various modifications and alterations may be implemented by those skilled in the art within the scope of the technical concept of the applied Claims, and these modifications and alterations are of course included in the technical scope of the disclosure.

For example, the tactile sensation presenting device 100 according to the present embodiment is not limited to the example of the application to the master-slave system. For example, the tactile sensation presenting device 100 may be applied to a medical instrument which the user actually holds to perform a medical operation. It should be noted that the tactile sensation presenting device 100 is not limited to an example of the application to the medical instrument, but may be applied to an arbitrary instrument.

Each device explained in the present description may be implemented as one device, or a part or all of the devices may be implemented as separate devices. For example, the master device 10, the slave device 20, the output device 30 and the control device 40 indicated in FIG. 1 may be implemented as one device. Further, the control device 40 indicated in FIG. 1 may be implemented as a server device which is connected with the master device 10, the slave device 20 and the output device 30 via a network or the like. It should be noted that the control device 40 may be disposed in at least one of the master device 10 and the slave device 20. The control unit 120 of the tactile sensation presenting device 100 indicated in FIG. 9 may also be disposed in at least one of the master device 10 and the control device 40.

A series of processing by each device explained in the present description may be implemented by software, by hardware or by a combination of software and hardware. The programs constituting the software are stored in a recording medium (non-transitory medium) which is disposed inside or outside each device. Each program is read into the RAM when the computer executes the program, and is executed by such as processor as a CPU.

The effects in the present description are merely explanatory or exemplary, and are not restrictive. In other words, the technique according to the present disclosure may exhibit other effects that are clear to those skilled in the art based on the description of the present description, along with the above mentioned effects or instead of the above mentioned effects.

The following configuration is also within a technical scope of the present disclosure.

(1)

A tactile sensation presenting device including: a plurality of tactile sensation presenting units configured to present a tactile sensation based on control information; and a control unit configured to generate the control information, which is different for each of the plurality of tactile sensation presenting units, based on information which is generated by an operation tool and is related to contact between the operation tool and an object, and to provide the control information to each of the plurality of tactile sensation presenting units.

(2)

The tactile sensation presenting device according to the above (1), wherein the control unit generates the control information in accordance with a perceptual characteristic of a region where each of the plurality of tactile sensation presenting units comes into contact.

(3)

The tactile sensation presenting device according to the above (2), wherein the information related to the contact includes first frequency and first displacement amount, the control information includes second frequency and second displacement amount, and based on the first frequency and first displacement amount, the control unit generates the control information such that at least either one of the second frequency or the second displacement amount is different from the first frequency or the second displacement amount.

(4)

The tactile sensation presenting device according to the above (3), wherein the control unit generates the control information such that the second frequency and the second displacement amount correspond to the frequency and displacement amount which is detectable by tactile receptors in a region where each of the plurality of the tactile sensation presenting units comes into contact.

(5)

The tactile sensation presenting device according to the above (4), wherein the control unit generates the plurality of control information such that at least one second frequency out of the second frequency of each of the plurality of control information is higher than a predetermined threshold.

(6)

The tactile sensation presenting device according to the above (4), wherein the control unit generates the plurality of control information so that at least one second frequency out of the second frequency of each of the plurality of control information is lower than a predetermined threshold.

(7)

The tactile sensation presenting device according to the above (4), wherein the control unit generates the control information such that at least one second frequency out of the second frequency of each of the plurality of control information is higher than a predetermined threshold, and at least one second frequency thereof is lower than a predetermined threshold.

(8)

The tactile sensation presenting device according to the above (7), wherein the control unit provides the control information, which includes the second frequency that is higher than the predetermined threshold, to the tactile sensation presenting unit disposed at a position where a vicinity of the finger tip of the user comes into contact, and provides the control information, which includes the second frequency that is lower than the predetermined threshold, to the tactile sensation presenting unit disposed at a position where a vicinity of the base of the finger of the user comes into contact.

(9)

The tactile sensation presenting device according to the above (4), wherein the control unit generates the plurality of control information such that the plurality of control information include the second frequency within a predetermined range.

(10)

The tactile sensation presenting device according to any one of the above (4) to (9), wherein the control unit generates the control information such that the second frequency is different from the first frequency, and the second displacement amount is equivalent to the first displacement amount.

(11)

The tactile sensation presenting device according to any one of the above (4) to (9), wherein the control unit generates the control information so that the second frequency and the second displacement amount are different from the first frequency and the first displacement amount respectively.

(12)

The tactile sensation presenting device according to any one of the above (2) to (11), wherein the control unit generates the control information in accordance with the perceptual characteristic of each user.

(13)

The tactile sensation presenting device according to any one of the above (1) to (12), wherein the information related to the contact and the control information further include direction information related to a direction corresponding to a direction of a contact force that is generated when the operation tool comes into contact with the object, and the plurality of tactile sensation presenting units present the tactile sensation in a direction indicated by the direction information.

(14)

The tactile sensation presenting device according to any one of the above (1) to (13), wherein the tactile sensation presenting device further comprises an acceleration sensor, and the control unit generates the control information in accordance with acceleration measured by the acceleration sensor.

(15)

The tactile sensation presenting device according to any one of the above (1) to (14), wherein the tactile sensation presenting device includes at least two tactile sensation presenting units, the first tactile sensation presenting unit is disposed in a vicinity of a first position, and the second tactile sensation presenting unit is disposed in a vicinity of a second position which is different from the first position.

(16)

The tactile sensation presenting device according to the above (15), wherein in a case where the shape of the tactile sensation presenting device is a needle holder shape, the first position is a position where the finger tip of the user comes into contact with the tactile sensation presenting device, and the second position is a position where the base of the finger of the user comes into contact with the tactile sensation presenting device.

(17)

The tactile sensation presenting device according to any one of the above (1) to (16), wherein a tactile sensation presenting unit, which is different from the plurality of tactile sensation presenting units, is further disposed outside the tactile sensation presenting device, and the control unit generates the control information in accordance with the different tactile sensation presenting unit, and provides the control information to the different tactile presenting unit.

(18)

A tactile sensation presenting system including:

a tactile sensation presenting device which includes a plurality of tactile sensation presenting units configured to present a tactile sensation based on control information, and a control unit configured to generate the control information, which is different for each of the plurality of tactile sensation presenting units, based on information which is generated by an operation tool and is related to contact between the operation tool and an object, and to provide the control information to each of the plurality of tactile sensation presenting units; a master device in which the tactile sensation presenting device is disposed; and a slave device in which the operation tool is disposed and which operates in accordance with operation of the master device by a user.

REFERENCE SIGNS LIST

10 Master device
20 Slave device
30 Output device
40 Control device
100 Tactile sensation presenting device
110 Communication device
120 Control unit
122 Signal processing unit
124 Driving control unit
130 Tactile sensation presenting unit
150 Force sensor
200 Medical instrument
210 Operation tool
1000 Master-slave system

The invention claimed is:

1. A tactile sensation presenting device, comprising:
a plurality of tactile sensation presenting units; and
a control unit configured to:
  receive information that includes
    a first frequency of vibration associated with an operation tool, and
    a first displacement amount of the vibration, wherein the received information is related to a first contact between the operation tool and an object;
  generate a plurality of pieces of control information different for the plurality of tactile sensation presenting units, based on
    the received information that includes the first frequency and the first displacement amount, and
    a perceptual characteristic of a first region of a user, wherein
      each of the plurality of tactile sensation presenting units is in a second contact with the first region,
      each piece of control information of the plurality of pieces of control information includes a second frequency and a second displacement amount,
      at least one of the second frequency is different from the first frequency or the second displacement amount is different from the first displacement amount, and
      a first piece of control information of the plurality of pieces of control information is different from a second piece of control information of the plurality of pieces of control information; and
  output the plurality of pieces of control information to the plurality of tactile sensation presenting units, wherein the plurality of tactile sensation presenting units is configured to present a tactile sensation based on the plurality of pieces of control information.

2. The tactile sensation presenting device according to claim 1, wherein the control unit is further configured to generate the plurality of pieces of control information such that the second frequency and the second displacement amount correspond to a third frequency and a third displacement amount which are detectable by tactile receptors in the first region.

3. The tactile sensation presenting device according to claim 2, wherein the control unit is further configured to generate the plurality of pieces of control information such that the second frequency of at least one piece of control information of the plurality of pieces of control information is higher than a detection threshold.

4. The tactile sensation presenting device according to claim 2, wherein the control unit is further configured to generate the plurality of pieces of control information so that the second frequency of at least one piece of control information of the plurality of pieces of control information is lower than a detection threshold.

5. The tactile sensation presenting device according to claim 2, wherein the control unit is further configured to generate the plurality of pieces of control information such that the second frequency of the first piece of control information is higher than a detection threshold, and the second frequency of the second piece of control information is lower than the detection threshold.

6. The tactile sensation presenting device according to claim 5, wherein
the control unit is further configured to:
  output, to a first tactile sensation presenting unit of the plurality of tactile sensation presenting units, the first piece of control information which includes the second frequency that is higher than the detection threshold; and
  output, to a second tactile sensation presenting unit of the plurality of tactile sensation presenting units, the second piece of control information which includes the second frequency that is lower than the detection threshold,
the first tactile sensation presenting unit is at a position where a vicinity of a finger tip of the user is in a third contact with the first tactile sensation presenting unit, and
the second tactile sensation presenting unit is at a position where a vicinity of a base of a finger of the user is in a fourth contact with the second tactile sensation presenting unit.

7. The tactile sensation presenting device according to claim 2, wherein the control unit is further configured to generate the plurality of pieces of control information such that the second frequency is within a specific range.

8. The tactile sensation presenting device according to claim 2, wherein the control unit is further configured to generate the plurality of pieces of control information such that the second frequency is different from the first frequency, and the second displacement amount is equivalent to the first displacement amount.

9. The tactile sensation presenting device according to claim 2, wherein the control unit is further configured to generate the plurality of pieces of control information so that the second frequency and the second displacement amount are different from the first frequency and the first displacement amount, respectively.

10. The tactile sensation presenting device according to claim 1, wherein
the control unit is further configured to generate the plurality of pieces of control information based on a perceptual characteristic of each user of a plurality of users,
the plurality of users includes the user, and
the perceptual characteristic of the user indicates a detection threshold related to a second vibration of tactile receptors of the user.

11. The tactile sensation presenting device according to claim 1, wherein
the received information further includes first direction information related to a first direction of a contact force,
the contact force is based on the first contact between the operation tool and the object,
the plurality of pieces of control information further includes second direction information related to a second direction corresponding to the first direction of the contact force, and
the plurality of tactile sensation presenting units is further configured to present the tactile sensation in the second direction based on the second direction information.

12. The tactile sensation presenting device according to claim 1, further comprising an acceleration sensor configured to measure an acceleration associated with the tactile sensation presenting device, wherein the control unit is further configured to generate the plurality of pieces of control information based on the acceleration measured by the acceleration sensor.

13. The tactile sensation presenting device according to claim 1, wherein
a first tactile sensation presenting unit of the plurality of tactile sensation presenting units is in a vicinity of a first position associated with the user,
a second tactile sensation presenting unit of the plurality of tactile sensation presenting units is in a vicinity of a second position associated with the user, and
the second position which is different from the first position.

14. The tactile sensation presenting device according to claim 13, wherein in a case where a shape of the tactile sensation presenting device is a needle holder shape,
the first position is a position where a finger tip of the user is in a third contact with the tactile sensation presenting device, and
the second position is a position where a base of a finger of the user is in a fourth contact with the tactile sensation presenting device.

15. The tactile sensation presenting device according to claim 1, wherein
the control unit is further configured to:
generate a third piece of control information of the plurality of pieces of control information based on a specific tactile sensation presenting unit; and
output the third piece of control information to the specific tactile sensation presenting unit,
the specific tactile sensation presenting unit is different from the plurality of tactile sensation presenting units, and
the specific tactile sensation presenting unit is outside of the tactile sensation presenting device.

16. A tactile sensation presenting system, comprising:
a master device that includes a tactile sensation presenting device, wherein the tactile sensation presenting device includes:
a plurality of tactile sensation presenting units; and
a control unit configured to:
receive information that includes
a first frequency of vibration associated with an operation tool, and
a first displacement amount of the vibration, wherein the received information is related to a first contact between the operation tool and an object;
generate a plurality of pieces of control information for the plurality of tactile sensation presenting units, based on
the received information that includes the first frequency and the first displacement amount, and
a perceptual characteristic of a region of a user, wherein
each of the plurality of tactile sensation presenting units is in a second contact with the region of the user,
each piece of control information of the plurality of pieces of control information includes a second frequency and a second displacement amount,
at least one of the second frequency is different from the first frequency or the second displacement amount is different from the first displacement amount, and
a first piece of control information of the plurality of pieces of control information is different from a second piece of control information of the plurality of pieces of control information; and
output the plurality of pieces of control information to the plurality of tactile sensation presenting units, wherein the plurality of tactile sensation presenting units is configured to present a tactile sensation based on the plurality of pieces of control information; and
a slave device that includes the operation tool, wherein the slave device is configured to execute a first operation based on a second operation of the user on the master device.

17. A tactile sensation presenting device, comprising:
a plurality of tactile sensation presenting units, wherein
a shape of the tactile sensation presenting device is a needle holder shape,
a first tactile sensation presenting unit of the plurality of tactile sensation presenting units is in a vicinity of a first position where a finger tip of a user is in a first contact with the tactile sensation presenting device,
a second tactile sensation presenting unit of the plurality of tactile sensation presenting units is in a vicinity of a second position where a base of a finger of the user is in a second contact with the tactile sensation presenting device, and
the second position is different from the first position; and
a control unit configured to:
receive information related to a third contact between an operation tool and an object;
generate a plurality of pieces of control information for the plurality of tactile sensation presenting units based on the received information, wherein a first piece of control information of the plurality of pieces of control information is different from a second piece of control information of the plurality of pieces of control information; and
output the plurality of pieces of control information to the plurality of tactile sensation presenting units, wherein the plurality of tactile sensation presenting units is configured to present a tactile sensation based on the plurality of pieces of control information.

* * * * *